United States Patent
Tardi et al.

(10) Patent No.: US 8,518,437 B2
(45) Date of Patent: *Aug. 27, 2013

(54) LIPID CARRIER COMPOSITIONS WITH ENHANCED BLOOD STABILITY

(75) Inventors: Paul Tardi, Surrey (CA); Murray Webb, North Vancouver (CA); Lawrence D. Mayer, North Vancouver (CA); Ludger M. Ickenstein, Vancouver (CA)

(73) Assignee: Celator Pharmaceuticals, Inc., Princeton, NJ (US)

( * ) Notice: Subject to any disclaimer, the term of this patent is extended or adjusted under 35 U.S.C. 154(b) by 1302 days.

This patent is subject to a terminal disclaimer.

(21) Appl. No.: 10/294,474

(22) Filed: Nov. 13, 2002

(65) Prior Publication Data

US 2003/0124181 A1 Jul. 3, 2003

Related U.S. Application Data

(60) Provisional application No. 60/394,271, filed on Jul. 9, 2002, provisional application No. 60/331,248, filed on Nov. 13, 2001.

(51) Int. Cl.
*A61K 9/127* (2006.01)

(52) U.S. Cl.
USPC .......................................................... 424/450

(58) Field of Classification Search
USPC .................... 424/450, 1.21, 9.321, 9.51, 417; 264/4.1, 4.3, 4.6
See application file for complete search history.

(56) References Cited

U.S. PATENT DOCUMENTS

| | | | |
|---|---|---|---|
| 4,756,910 A | 7/1988 | Yagi et al. | 424/450 |
| 4,769,250 A | 9/1988 | Forssen | 424/450 |
| 4,895,719 A * | 1/1990 | Radhakrishnan et al. | 424/45 |
| 4,915,951 A | 4/1990 | Baldeschwieler et al. | 424/450 |
| 4,927,571 A | 5/1990 | Huang et al. | |
| 5,077,056 A | 12/1991 | Bally et al. | 424/450 |
| 5,225,212 A | 7/1993 | Martin et al. | 424/450 |
| 5,393,530 A | 2/1995 | Schneider et al. | |
| 5,415,869 A | 5/1995 | Straibinger et al. | 424/450 |
| 5,773,027 A * | 6/1998 | Bergeron et al. | 424/450 |
| 5,817,334 A * | 10/1998 | Schmidt et al. | 424/450 |
| 5,843,473 A * | 12/1998 | Woodle et al. | 424/450 |
| 5,888,473 A * | 3/1999 | Hawthorne et al. | 424/1.21 |

(Continued)

FOREIGN PATENT DOCUMENTS

| | | |
|---|---|---|
| EP | 0 804 925 | 11/1997 |
| GB | 2256139 | 12/1992 |

(Continued)

OTHER PUBLICATIONS

Ahl, P. L., et al., "Enhancement of the In Vivo Circulation Lifetime of L-α-Distearoylphosphatidylcholine Liposomes: Importance of Liposomal Aggregation Versus Complement Opsonization" Biochim. Biophys. Acta (1997) 1329:370-382.

(Continued)

*Primary Examiner* — Gollamudi Kishore
(74) *Attorney, Agent, or Firm* — Morrison & Foerster LLP

(57) ABSTRACT

Liposomes that contain at least 10 mol % of a negatively charged lipid coupled to a non-zwitterionic moiety are stable in the blood. Liposomes containing at least 1 mol % of such lipids may be frozen safely.

1 Claim, 22 Drawing Sheets

(56) References Cited

U.S. PATENT DOCUMENTS

| | | | |
|---|---|---|---|
| 5,945,122 A * | 8/1999 | Abra et al. | 424/450 |
| 5,965,156 A * | 10/1999 | Proffitt et al. | 424/450 |
| 6,120,800 A * | 9/2000 | Forssen et al. | 424/450 |
| 6,139,871 A | 10/2000 | Hope et al. | 424/450 |
| 6,200,598 B1 * | 3/2001 | Needham | 424/450 |
| 6,270,806 B1 | 8/2001 | Liversidge et al. | |
| 6,623,753 B1 * | 9/2003 | Bodmer et al. | 424/450 |
| 6,679,822 B2 | 1/2004 | Kubo et al. | |

FOREIGN PATENT DOCUMENTS

| | | |
|---|---|---|
| JP | 07-316041 | 12/1995 |
| JP | 11-171772 | 6/1999 |
| JP | 2001-026544 | 1/2001 |
| JP | 2001-302496 | 10/2001 |
| JP | 2002-363278 | 12/2002 |
| WO | WO-95/15762 | 6/1995 |
| WO | WO-99/27908 | 6/1999 |
| WO | WO 99/59547 | 11/1999 |
| WO | WO 01/05372 | 1/2001 |

OTHER PUBLICATIONS

Akhtar, S., et al., "Interactions of Antisense DNA Oligonucleotide Analogs with Phospholipid Membranes (Liposomes)" Nucleic Acids Res. (1991) 19:5551-5559.

Allen, et al., "Phosphatidylserine as a Determinant of Reticuloendothelial Recognition of Liposome Models of the Erythrocyte Surface" Proc. Natl. Acad. Sci. USA (1998) 85:8061-8071.

Bendas, et al., "Synthetic Glycolipids as Membrane-Bound Cryoprotectants in the Freeze-drying Process of Liposomes" Eur. J. Pharma. Sci. (1996) 4:211-222.

Brodt, P., et al., "Inhibition of Murine Hepatic Tumor Growth by Liposomes Containing a Lipophilic Muramyl Dipeptide" Cancer Immunol. Immunother. (1989) 28:54-58.

Farmer, M. C., et al., "Liposome-Encapsulated Hemoglobin as an Artificial Oxygen-Carrying System" Meth. Enzymol. (1987) 149:184-200.

Goodrich, et al., "Alterations in Membrane Surfaces Induced by Attachment of Carbohydrates" Biochemistry (1991) 30:5313-5318.

Kao, Y, et al., "Pharmacological Disposition of Negatively Charged Phospholipid Vesicles in Rats" J. Pharm. Sci. (1980) 69:1338-1349.

Kirby, et al., "Effect of the Cholesterol Content of Small Unilamellar Liposomes on their Stability In Vivo and In Vitro" Biochem. J. (1980) 186:591-598.

Ogihara-Umeda, I., et al., "Cholesterol Enhances the Delivery of Liposome-encapsulatedr Gallium-67 to Tumors" Eur. J. Nucl. Med. (1989) 15:617.

Canadian Office Action for Application No. 2,467,064, date mailed on Jul. 12, 2007, 6 pages.

Notice of Reasons for Rejection for Japanese Patent Application No. 2003-543568, mailed on Apr. 21, 2009, 8 pages.

International Search Report for PCT/CA02/01726, date mailed on Jul. 29, 2003, 4 pages.

* cited by examiner

LIPID CARRIER COMPOSITIONS WITH ENHANCED BLOOD STABILITY

CROSS-REFERENCE TO RELATED APPLICATIONS

This application claims benefit of U.S. Serial No. 60/394,271, filed Jul. 9, 2002, and of U.S. Serial No. 60/331,248, filed 13 Nov. 2001. The contents of these applications are incorporated herein by reference.

TECHNICAL FIELD

The present invention relates to liposomal compositions having long lifetime in circulation. These liposomes include the incorporation of negatively charged lipids that do not include zwittenrions.

BACKGROUND ART

Liposomes are delivery vehicles prepared from aqueous dispersions of amphipathic lipids arranged in one or more bilayers around a central aqueous core. Solutes may be entrapped in the internal aqueous compartment thereby protecting them from reaction with blood components. In order to effectively deliver an entrapped agent to a target site, it is desirable that a liposome exhibits optimal circulation longevity and retention of an encapsulated agent.

The pharmacological properties of liposomes may be varied by changing the types of lipids incorporated in the membrane. Liposomes composed of neutral (no net charge) lipids are commonly employed as such liposomes are stable upon exposure to the numerous protein, carbohydrate and lipid components present in the blood compartment. Incorporating negatively charged lipids such as phosphatidylserine in liposomal compositions has resulted in increased recognition and clearance of liposomes from the circulation. Kirby, et al., *Biochem. J.* (1980) 186:591-598. Thus, drug delivery to disease sites is reduced. Allen, et al. *Proc. Natl. Acad. Sci. USA* (1998) 85:8061-8071.

A comparison of the circulation lifetimes of liposomes containing phosphatidylinositol, phosphatidylglycerol, cardiolipin and phosphatidylserine revealed that phosphatidylserine liposomes were eliminated quickly from the circulation whereas cardiolipin, phosphatidylglycerol and phosphatidylinositol liposomes were eliminated at a reduced rate in rats (Kao, Y, et al., *J. Pharm. Sci.* (1980) 69:1338-1349).

Although it has been acknowledged that certain negatively charged liposomes may have utility in in vivo applications, the use of these lipids to confer long-circulating properties has only recently been recognized. WO99/59547. These studies have revealed that the incorporation of phosphatidylglycerol into cholesterol/DPPC containing liposomes led to enhanced blood stability. These investigations also revealed, however, that the mol % incorporation of the lipid dimyristoylphosphatidylglycerol (DMPG) had an influence on the circulation properties of the carrier as cholesterol/DPPC liposomes prepared with less than 10 mol % DMPG exhibited increased blood stability properties in relation to those prepared with greater than 10 mol % DMPG. It was also noted that lipid components such as distearoylphosphatidylcholine (DSPC) and dimyristoyl-phosphatiylcholine (DMPC) possess undesirable properties and thus were not included in these formulations.

Liposomal preparations which contain phosphatidyl glycerol in addition to additional vesicle-forming lipids are described in Brodt, P., et al., *Cancer Immunol. Immunother.* (1989) 28:54-58 and by Hope, et al., U.S. Pat. No. 6,139,871. In these preparations, however, the negatively charged lipid coupled to a hydrophilic portion which is non-zwitterionic, exemplified by PG, is present in an amount less than 10 mol %. Similarly, the liposomes described in WO99/59547 include less than 10 mol % PG. The liposomes described by Akhtar, S., et al., *Nucleic Acids Res.* (1991) 19:5551-5559 and by Ahl, P. L., et al., *Biochim. Biophys. Acta* (1997) 1329:370-382 and by Farmer, M. C., et al., *Meth. Enzymol.* (1987) 149:184-200 contain substantial amounts of cholesterol, unlike the liposomes of the present invention. In addition, the liposomes of Akhtar exhibit transition temperatures lower than 38° C. as the acyl chains contained in the phospholipids employed contain less than 18 carbon atoms.

U.S. Pat. No. 5,415,869 describes taxol formulations contained in liposomes which may contain phosphatidylcholines and phosphatidyl glycerols. There is no suggestion that the liposomes have extended circulation lives, nor is it indicated that transition temperatures above 38° C. are preferred.

U.S. Pat. No. 4,769,250 describes formulations made from mixtures of anionic and neutral phospholipids including DSPG and DSPC; however, these liposomes are SUVs with dimensions of 45-55 nm.

Cryoprotectants have been added to liposome preparations in order to prevent the detrimental effects due to freezing and freeze-drying (lyophilization). Disaccharides such as trehalose, sucrose, lactose, sorbitol, mannitol, sucrose, maltodextrin and dextran are the most commonly used cryoprotectants (see WO01/05372 and U.S. Pat. No. 5,077,056).

Membrane-bound cryoprotectants have been utilized with the goal of further improving resistance to freezing and freeze-drying damage. In particular, sugars attached to liposomal membrane surfaces via oligo(ethylene oxide) linkers consisting of one to three repeating units have been reported to be cryoprotective (Bendas, et al., *Eur. J. Pharma. Sci.* (1996) 4:211-222; Goodrich, et al., *Biochemistry* (1991) 30:5313-5318; U.S. Pat. No. 4,915,951). Baldeschwieler, et al., reported that in the absence of the terminal sugar group, liposomes prepared with the oligoethylene oxide linker itself were unable to protect against fusion subsequent to freezing (see U.S. Pat. No. 4,915,951).

Inclusion of cholesterol in liposomal membranes has been shown to reduce release of drug after intravenous administration (for example, see: U.S. Pat. Nos. 4,756,910, 5,077,056, and 5,225,212; Kirby, C., et al., *Biochem. J.* (1980) 186:591-598; and, Ogihara-Umeda, I., et al., *Eur. J. Nucl. Med.* (1989) 15:617). Generally, cholesterol increases bilayer thickness and fluidity while decreasing membrane permeability, protein interactions, and lipoprotein destabilization of the liposome. Conventional approaches to liposome formulation dictate inclusion of substantial amounts (e.g., 30-45 mol %) cholesterol or equivalent membrane rigidification agents (such as other sterols) into liposomes.

DISCLOSURE OF THE INVENTION

This invention therefore provides a liposome comprising: a negatively charged lipid having a hydrophilic portion and a hydrophobic portion with a neutral non-zwitterionic moiety attached to the hydrophilic portion of the lipid. In particular embodiments, liposomes of this invention are substantially free of cholesterol. The liposomes will typically contain a biologically active agent. Liposomes of the invention surprisingly exhibit enhanced circulation longevity in the bloodstream.

The negatively charged lipid is typically a phospholipid or a sphingophospholipid. Preferably, the lipid is a phospholipid; i.e., a glycerol to which two acyl groups are attached and wherein the third hydroxyl is coupled to a phosphate. The non-zwitterionic moiety is attached to this negatively charged lipid, preferably to the phosphate group. Preferably, the non-zwitterionic moiety is neutral such that the net negative charge on a lipid used in this invention is due solely to the negative charge of the lipid component.

The non-zwitterionic moiety may comprise functional groups that impart a desired hydrophilicity to the lipid, such groups being selected from alcohols, ketones, carboxylic acids, ethers and amines. A preferred non-zwitterionic moiety is a short-chain alcohol such as glycerol, or a cyclic alcohol, such as inositol, or a polyalkylene oxide such as PEG.

In one embodiment, the liposomes comprise greater than 10 mol % of one or more of said aggregation preventing lipids—i.e., the negatively charged lipids comprising a non-zwitterionic moiety, as described above; and up to 90 mol % of one or more vesicle-forming lipids, wherein the liposome contains substantially no cholesterol. Preferably, the non-zwitterionic moiety is a short-chain alcohol such as glycerol, or is a cyclitol such as inositol, or a polyalkylene oxide. Most preferably, the vesicle-forming lipids making up the liposome are selected such that the phase transition temperature of the liposome is greater than at least 38° C., preferably at least 40° C. Preferably, the dimensions of the liposomes are of the order 80-200 nm±25 nm. With regard to protection against damage by freezing, as little as 1 mol % of the aggregation preventing lipid may be present.

For storage, the liposomes of the invention may be frozen or lyophilized, and may comprise cryoprotectants. The amount of cryoprotectant used depends on the type of cryoprotectant and the characteristics of the liposome to be protected. Persons skilled in the art can readily test various cryoprotectant types and concentrations to determine which cryoprotectant type and concentration works best for a particular liposome preparation. In general, sugar concentrations on the order of 100 mM and above have been found necessary to achieve the highest level of protection. In terms of moles of membrane phospholipid, millimolar levels on the order of 100 mM correspond to approximately 5 moles of sugar per mole of phospholipid.

Liposomes of the invention may comprise substantially no cryoprotectant. The term "substantially no cryoprotectant" refers to liposomes comprising less than 20 mM of a cryoprotectant or less than 10 mM cryoprotectant. In the case where different concentrations of cryoprotectant are present in the interior and exterior of the liposome, the highest concentration present in the exterior or interior is taken as concentration referred to in the these definitions.

In the event the liposomes of the invention are to be frozen, it is preferred, but not required, that the liposomes be substantially free of cholesterol and comprise hydrophilic polymer lipid conjugates, particularly those greater than about 125 daltons as these liposomes are resistant to fusion and leakage of agent subsequent to freezing. Thus, if the liposomes are to be frozen, they will contain about 1-30 mol % of one or more hydrophilic polymer-conjugated lipids and up to about 99 mol % of one or more vesicle-forming lipids, and substantially no cholesterol. Preferably, the hydrophilic polymer-lipid conjugate is a PEG lipid conjugate. The liposomes may also contain cryoprotectants such as trehalose, maltose, sucrose, glucose, lactose, dextran or aminoglycosides. Particularly preferred is glucose.

The liposomes may be frozen to about −5° C., preferably below about −10° C. and more preferably below about −20° C. They may be lyophilized when frozen.

DSPE-PEG2000 (95:5 mol %), DSPC/cholesterol (55:45 mol %) and DSPC/cholesterol/DSPE-PEG2000 (50:45:5 mol %) were tested.

Figure 9:
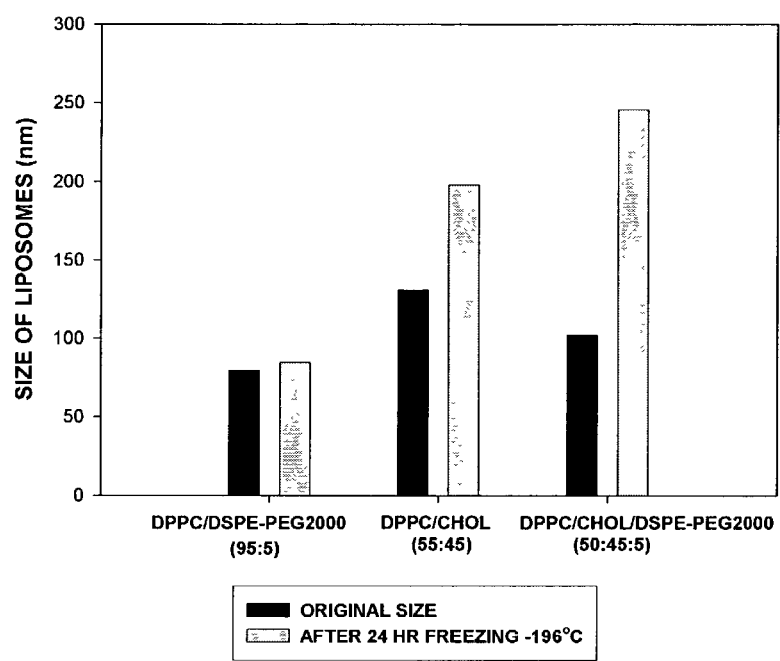

FIG. 9 is a histogram showing the size of liposomes containing HBS both inside and outside the liposomal membrane prior to (black bar) and subsequent to (grey bar) 24 hour freezing. Liposomes consisting of DPPC/DSPE-PEG2000 (95:5 mol %), DPPC/cholesterol (55:45 mol %) and DPPC/cholesterol/DSPE-PEG2000 (50:45:5 mol %) were tested.

Figure 10:
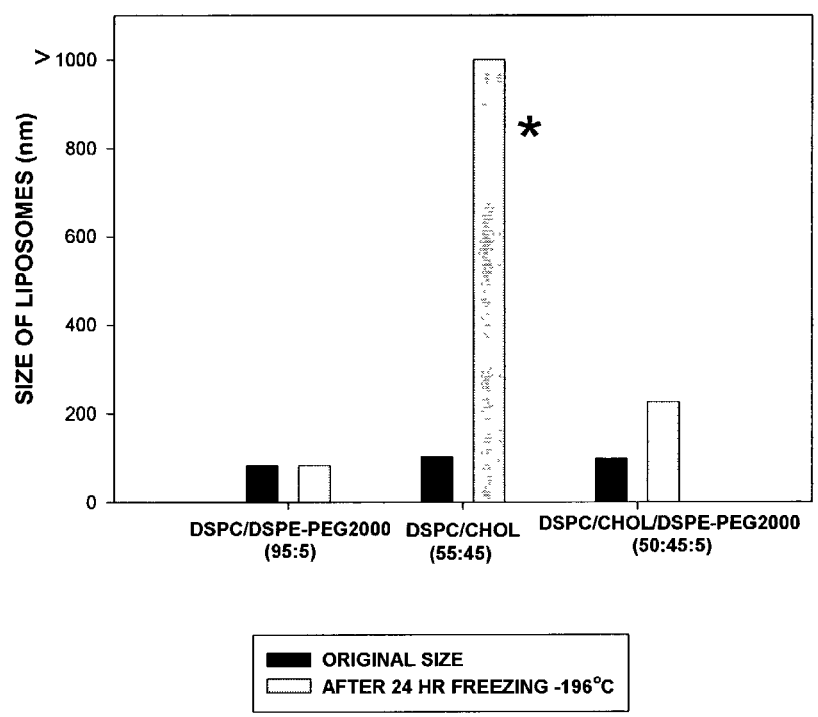

FIG. 10 is a histogram showing the size of liposomes containing HBS both inside and outside the liposomal membrane prior to (black bar) and subsequent to (grey bar) 24 hour freezing. Liposomes consisting of DSPC/DSPE-PEG2000 (95:5 mol %), DSPC/cholesterol (55:45 mol %) and DSPC/cholesterol/DSPE-PEG2000 (50:45:5 mol %) were tested.

Figure 11:
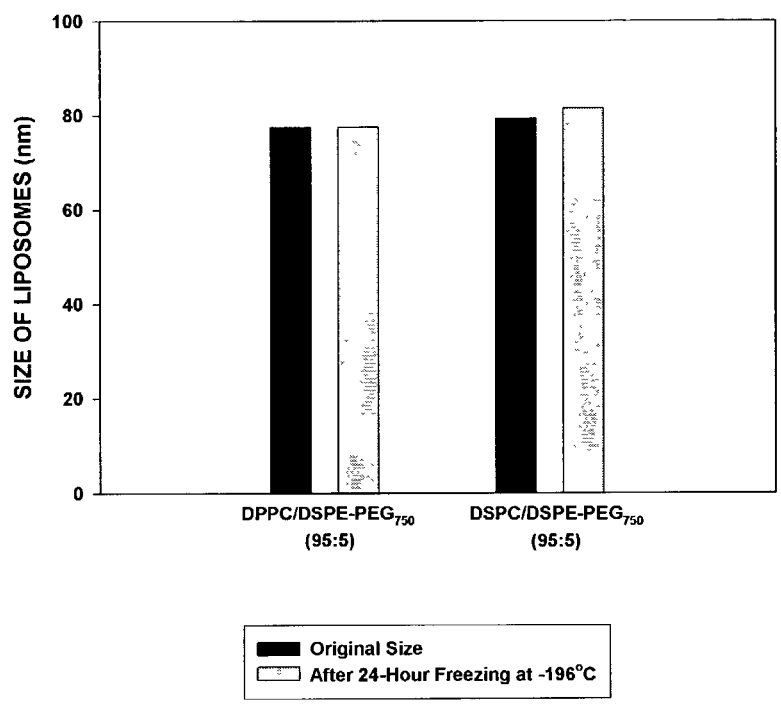

FIG. 11 is a histogram showing the size of liposomes containing HBS both inside and outside the liposomal membrane prior to (black bar) and subsequent to (grey bar) 24 hour freezing. Liposomes consisting of DPPC/DSPE-PEG750 (95:5 mol %) and DSPC/DSPE-PEG750 (95:5 mol %) were tested.

Figure 12:
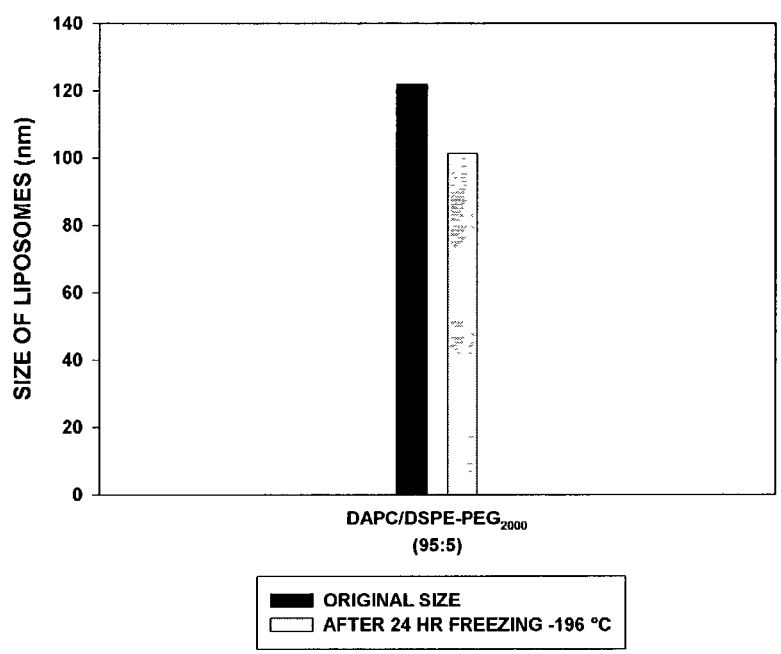

FIG. 12 is a histogram showing the size of liposomes prior to (black bar) and subsequent to (grey bar) 24 hour freezing. Liposomes consisting of DAPC/DSPE-PEG2000 (95:5 mol %) were tested.

Figure 13:
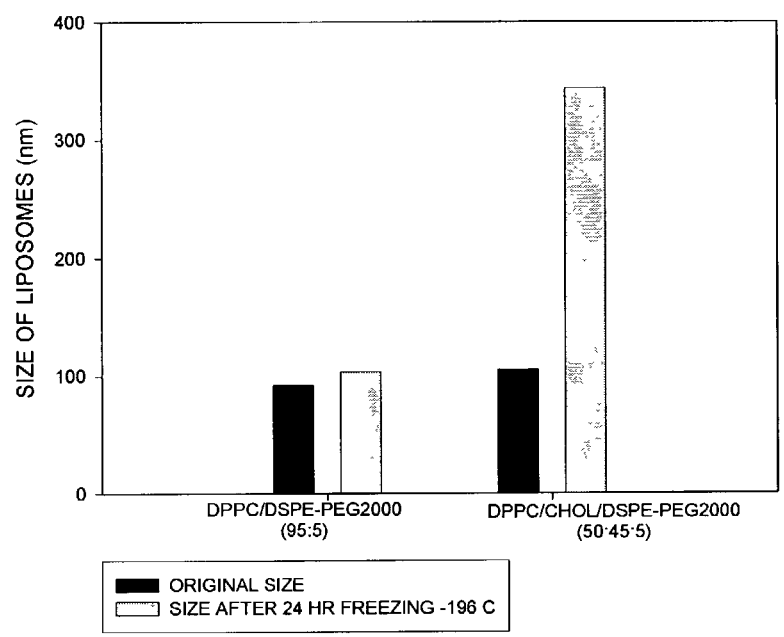

FIG. 13 is a histogram showing the size of liposomes containing citrate pH 4.0 inside and HBS outside the liposomal membrane prior to freezing (black bar) and subsequent to freezing (grey bar) for 24 hours. Liposomes consisting of DPPC/DSPE-PEG2000 (95:5 mol %) and DPPC/cholesterol/DSPE-PEG2000 (50:45:5 mol %) were tested.

Figure 14:
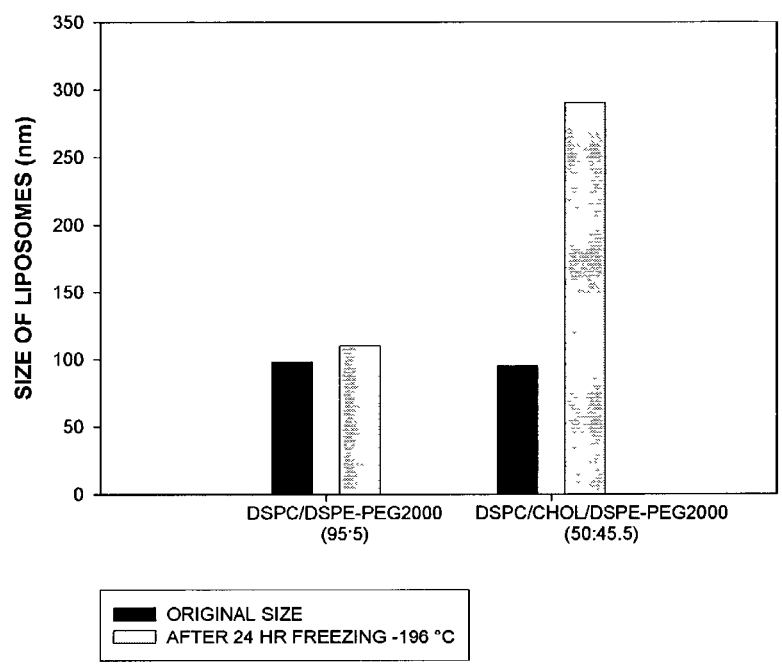

FIG. 14 is a histogram showing the size of liposomes containing citrate pH 4.0 inside and HBS outside the liposomal membrane prior to (black bar) freezing and subsequent to (grey) freezing for 24 hours. Liposomes consisting of DSPC/DSPE-PEG2000 (95:5 mol %) and DSPC/cholesterol/DSPE-PEG2000 (50:45:5 mol %) were tested.

Figure 15:
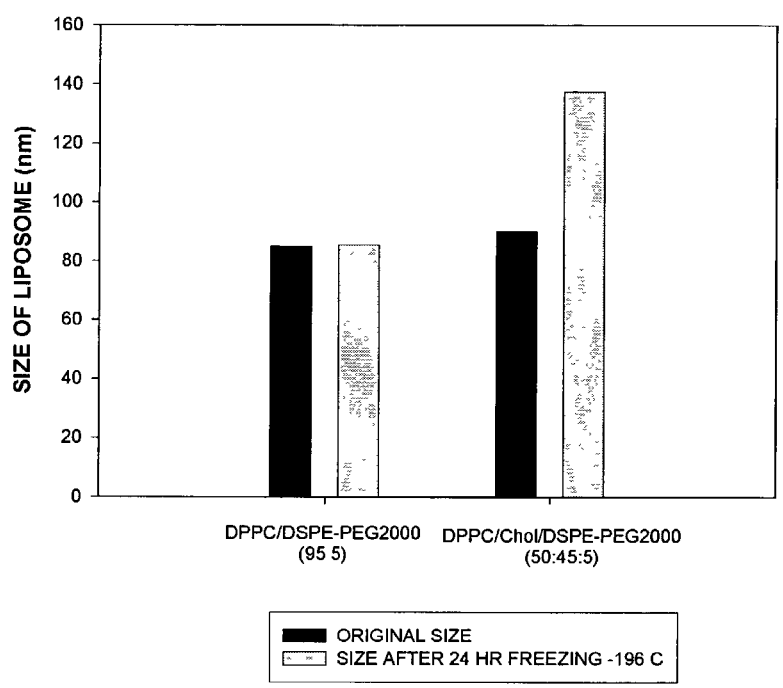

FIG. 15 is a histogram showing the size of liposomes containing entrapped glucose prior to freezing (black bar) and subsequent to freezing (grey bar) for 24 hours. Liposomes consisting of DPPC/DSPE-PEG2000 (95:5 mol %) and DPPC/cholesterol/DSPE-PEG2000 (50:45:5 mol %) were tested.

Figure 16:
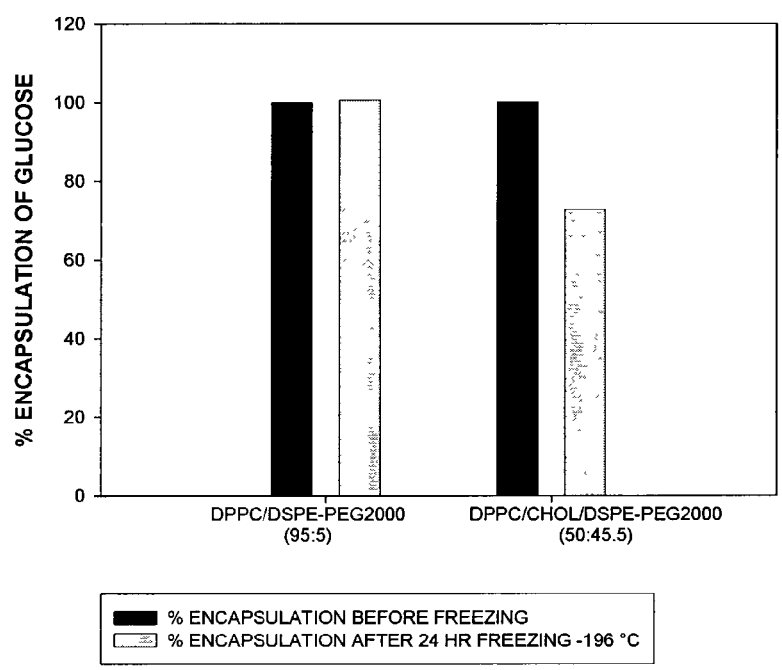

FIG. 16 is a histogram showing the percent of encapsulation of glucose in liposomes prior to freezing (black bar) and subsequent to freezing (grey bar) for 24 hours. Liposomes consisting of DPPC/DSPE-PEG2000 (95:5 mol %) and DPPC/cholesterol/DSPE-PEG2000 (50:45:5 mol %) were tested.

Figure 17:
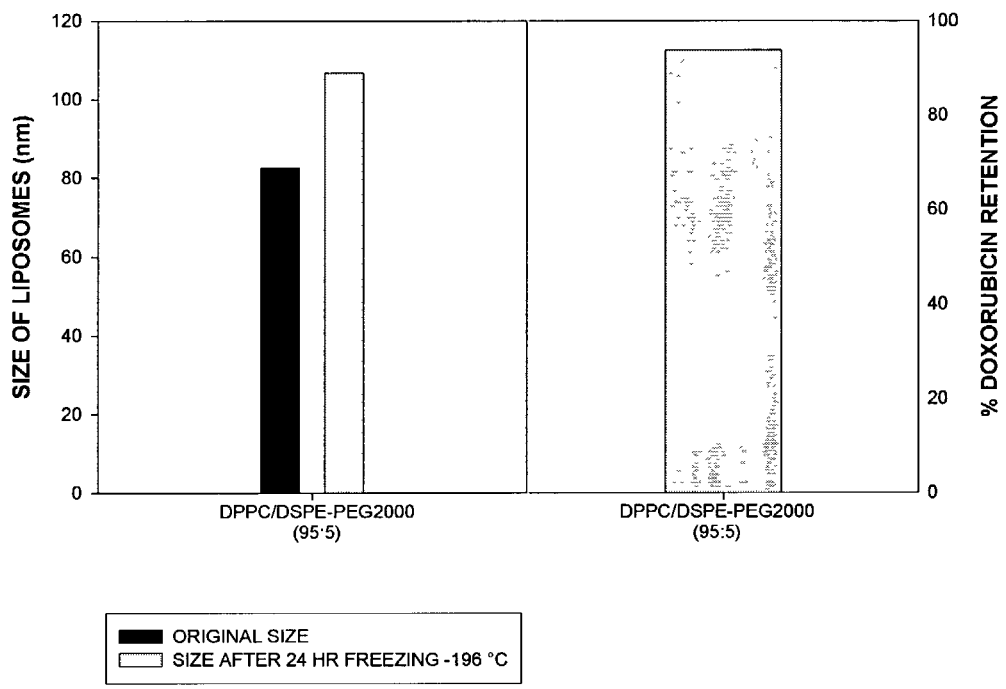

FIG. 17 is a histogram showing the size of DPPC/DSPE-PEG2000 liposomes containing entrapped doxorubicin prior to freezing (black bar) and subsequent to freezing (grey bar) for 24 hours (left panel) and percent doxorubicin retention (right panel).

Figure 18:
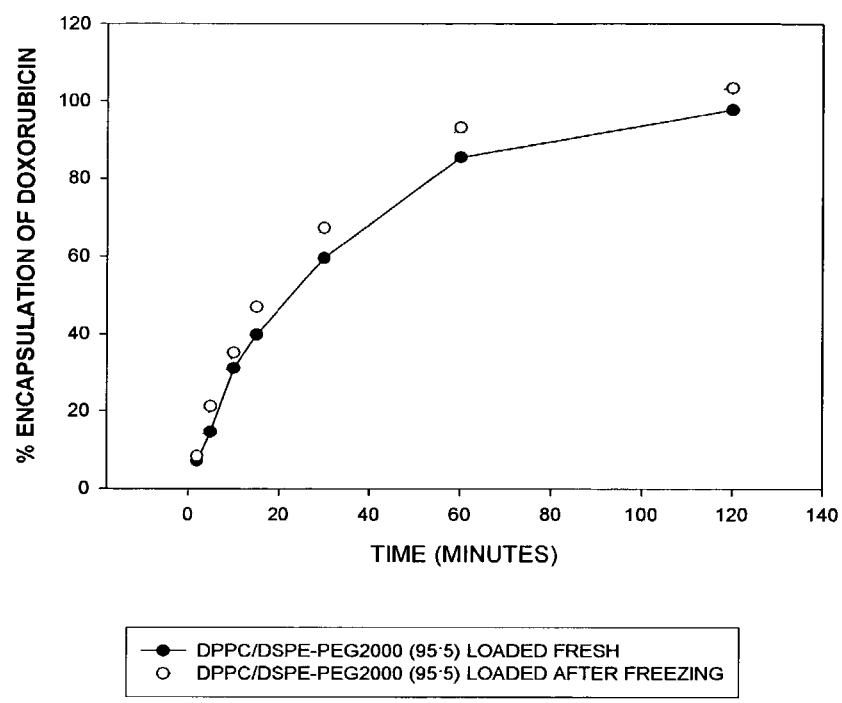

FIG. 18 is a graph showing the percent encapsulation of doxorubicin in DPPC/DSPE-PEG2000 (95:5 mol %) liposomes during loading as a function of time. Loading was performed prior to freezing (filled circles) and subsequent to freezing (open circles).

Figure 19:
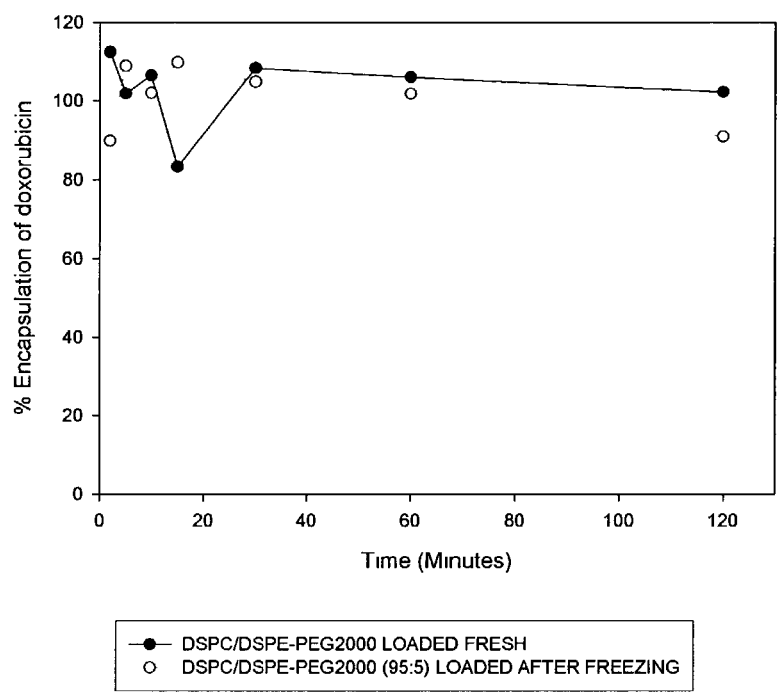

FIG. 19 is a graph showing the percent encapsulation of doxorubicin in DSPC/DSPE-PEG2000 (95:5 mol %) liposomes during loading as a function of time. Loading was performed prior to freezing (filled circles) and subsequent to freezing (open circles).

MODES OF CARRYING OUT THE INVENTION

"Liposome" as used herein means vesicles comprised of one or more concentrically ordered lipid bilayers encapsulating an aqueous phase. Formation of such vesicles requires the presence of "vesicle-forming lipids" which are amphipathic lipids capable of assuming or being incorporated into a bilayer structure. This includes such lipids that are capable of forming a bilayer by itself or when in combination with another lipid or lipids. An amphipathic lipid is incorporated into a lipid bilayer by having its hydrophobic moiety in contact with the interior, hydrophobic region of the bilayer membrane and its polar head moiety oriented towards an outer, polar surface of the membrane. Most phospholipids belong to the former type of vesicle forming lipid whereas cholesterol is a representative of the latter type.

Suitable vesicle-forming lipids that may be incorporated into liposomes or lipid carriers of this invention may be selected from a variety of amphiphatic lipids, typically including phospholipids such as phosphatidylcholine (PC) and, sphingolipids such as sphingomyelin. In this specification, the terms "bulk" or "structural" with reference to a lipid means a vesicle-forming lipid which contributes to structure of a liposome.

Liposomes prepared in accordance with this invention can be prepared by conventional techniques used to prepare vesicles. These techniques include the ether injection method (Deamer, et al., *Acad. Sci.* (1978) 308:250), the surfactant method (Brunner, et al., *Biochim. Biophys. Acta* (1976) 455: 322), the freeze-thaw method (Pick, et al., *Arch. Biochim. Biophys.* (1981) 212:186) the reverse-phase evaporation method (Szoka, et al., *Biochim. Biophys. Acta* (1980) 601: 559-571), the ultrasonic treatment method (Huang, et al., *Biochemistry* (1969) 8:344), the ethanol injection method (Kremer, et al., *Biochemistry* (1977) 16:3932) the extrusion method (Hope, et al., *Biochim. Biophys. Acta* (1985) 812:55-65) and the French press method (Barenholz, et al., *FEBS Lett.* (1979) 99:210). These processes can be used in combination or modified. Small unilamellar vesicles (SUVs) can be prepared by the ultrasonic treatment method, the ethanol injection method and the French press method. Preferably, multilamellar vesicles (MLVs) are prepared by the reverse-phase evaporation method or by the simple addition of water to a lipid film followed by dispersal by mechanical agitation (Bangham, et al., *J. Mol. Biol.* (1965) 13:238-252).

A particularly suitable liposome preparation which may be used in the practice of this invention are large unilamellar vesicles (LUVs). LUVs may be prepared by the ether injection method, the surfactant method, the freeze-thaw method, the reverse-phase evaporation method, the French press method or the extrusion method. Preferably, LUVs are prepared according to the extrusion method. The extrusion method involves first combining lipids in chloroform to give a desired molar ratio. A lipid marker may optionally be added to the lipid preparation. The resulting mixture is dried under a stream of nitrogen gas and placed in a vacuum pump until the solvent is substantially removed. The samples are then hydrated in an appropriate buffer or mixture of therapeutic agent or agents. The mixture is then passed through an extrusion apparatus to obtain liposomes of a defined average size. Average liposome size can be determined by quasi-elastic light scattering using, for example, a NICOMP™ 370 submicron particle sizer at a wavelength of 632.8 nm.

Liposomes that contain "substantially no cholesterol" may contain an amount of cholesterol that is insufficient to significantly alter the phase transition characteristics of the liposome (typically less than 20 mol % cholesterol). 20 mol % or more of cholesterol broadens the range of temperatures at which phase transition occurs, with phase transition disappearing at higher cholesterol levels. Preferably, a liposome having substantially no cholesterol will have about 15 or less and more preferably about 10 or less mol % cholesterol, more preferably about 5 or less mol %, or about 2 or less mol % or about 1 or less mol % cholesterol. Also, no cholesterol may be present or added when preparing "cholesterol-free" liposomes.

The terms "lipid that is negatively charged at physiological pH" or "negatively charged lipid" refer to vesicle-forming lipids having one or more negative charges at physiological pH. Suitable negatively charged lipids for use in this invention may be phospholipids or phosphosphingolipids. Negatively charged lipids comprising non-zwitterionic moieties may be incorporated in the liposome at 5 to 95 mol %, more preferably at 10 to 50 mol % and most preferably at 15 to 30 mol %. The "non-zwitterionic moiety" refers to a moiety that does not have opposing charges at physiological pH, but is hydrophilic.

The net negative charge on a lipid used in this invention may arise solely from the presence of the charge on the negatively charged lipid (e.g., on the phosphate group) or additional negative charge may be due to the presence of one or more negatively charged groups residing on the non-zwitterionic moiety. Preferably, the net negative charge arises solely from the presence of one or more negatively charged groups on the lipid, in which case the non-zwitterionic moiety is a neutral group. Preferably, the non-zwitterionic moiety comprises 2 to 6 carbon atoms.

Suitable non-zwitterionic moieties contain electron-withdrawing functional groups that impart to the head group hydrophilic characteristics. Such functional groups can be selected from the group consisting of alcohols, acids, ketones, esters, ethers, amides and aldehydes. Saccharides may also be used in this regard.

Monosaccharides include arabinose, fucose, galactose, glucose, lyxose, mannose, ribose and xylose. Disaccharides include sucrose, lactose, trehalose, cellobiose, gentiobiose and maltose. Monosaccharides and disaccharides which do not bind to cellular receptors are preferred since increased clearance of the liposomes from the circulation may result from the binding of the liposome to a cell surface.

When the non-zwitterionic moiety is selected to be neutral at physiological pH, the incorporation of non-ionizable groups such as alcohols, ketones, esters, ethers, amides and aldehydes are chosen.

In one embodiment of the invention, the non-zwitterionic moiety is a short-chain alcohol, a preferred alcohol containing two or more hydroxyl groups. The alcohol can be a straight-chain polyol of which glycerol is an example, which is attached to a phosphate of a phospholipid via a terminal hydroxyl group of the glycerol molecule, the resulting molecule being termed a phosphatidylglycerol (PG). Preferably the fatty acid chains of the phosphatidylglycerol are independently caproyl (6:0), octanoyl (8:0), capryl (10:0), lauroyl (12:0), myristoyl (14:0), palmitoyl (16:0), stearoyl (18:0), arachidoyl (20:0), behenoyl (22:0), lingnoceroyl (24:0) or phytanoyl, including the unsaturated versions of these fatty acid chains in the cis or trans configurations such as oleoyl (18:1), linoleoyl (18:2), arachidonoyl (20:4) and docosahexaenoyl (22:6). Phospholipids having two acyl chains of 14 to 18 carbon atoms are preferred. In any event, in one embodiment, the nature of the hydrophobic substituents of the negatively charged lipid is such that the phase transition temperature of the liposome is greater than about 38° C., preferably greater than about 40° C.

In another embodiment, the non-zwitterionic moiety is a ring structure, preferably a cyclitol. Such compounds may be derivatized with various groups to impart to the molecule a desired water solubility. Preferably the cyclitol is an inositol attached to a phospholipid through the phosphate group, the resulting compound being phosphatidylinositol. Preferably, the fatty acid chains of the phosphatidylinositol are selected independently and are as described above.

In another embodiment, the non-zwitterionic moiety may be a polymer to form a "hydrophilic polymer-lipid conjugate." This refers to a vesicle-forming lipid covalently joined at its polar head moiety to a hydrophilic polymer, and is typically made from a lipid that has a reactive functional group at the polar head moiety in order to attach the polymer. Suitable reactive functional groups are for example, amino, hydroxyl, carboxyl or formyl. The lipid may be any lipid described in the art for use in such conjugates such as phospholipids, sphingolipids and ceramides. Preferably, the lipid is a phospholipid such as PC, PE, PA or PI, having two acyl chains comprising between about 6 to about 24 carbon atoms in length with varying degrees of unsaturation. The lipid in the conjugate may, for example, be a PE, preferably of the distearoyl form. The polymer is a biocompatible polymer characterized by a solubility in water that permits polymer chains to effectively extend away from a liposome surface with sufficient flexibility that produces uniform surface coverage of a liposome. Preferably, the polymer is a polyalkylether, including polymethylene glycol, polyhydroxy propylene glycol, polypropylene glycol, polylactic acid, polyglycolic acid, polyacrylic acid and copolymers thereof, as well as those disclosed in U.S. Pat. Nos. 5,013,556 and 5,395,619. A preferred polymer is polyethylene glycol (PEG). The conjugate may be prepared to include a releasable lipid-polymer linkage such as a peptide, ester, or disulfide linkage. The conjugate may also include a targeting ligand. Mixtures of conjugates may be incorporated into liposomes for use in this invention.

The term "PEG-conjugated lipid" as used herein refers to the above-defined hydrophilic polymer-lipid conjugate in which the polymer is PEG.

A hydrophilic polymer-lipid conjugate or other non-zwitterion-containing negatively charged lipid may be prepared to include a releasable lipid-polymer linkage such as a peptide, ester or disulfide linkage which can be cleaved under selective physiological conditions so as to expose an LUV carrier surface once a desired biodistribution has been achieved, such as is disclosed in U.S. Pat. No. 6,043,094; or, in Kirpotin, D., et al., *FEBS Letters* (1996) 388:115-188.

A hydrophilic polymer-lipid conjugate may also include a targeting ligand attached at the free end of the polymer to direct the liposome to specific cells. Derivatives of polyethyleneglycol that allow conjugation of a targeting ligand are for example, methoxy(hydrazido)polyethyleneglycol and bis(hydrazido)polyethyleneglycol.

Negatively charged lipids may be obtained from natural sources or may be chemically synthesized. Methods to covalently attach compounds to the head group of a lipid are well known in the art and generally involve reacting functional groups on the terminal portion of the lipid head group with functional groups on the moiety to be attached. Suitable negatively charged lipids for the chemical attachment of a non-zwitterionic hydrophilic moiety include lipids having a polar head group that terminates with a reactive functional group such as phosphate, an amine. An example of a particularly suitable lipid is a phosphatidylethanolamine as it contains a reactive amino group. Methods for preparing phosphatidylethanolamine derivatives have been described in Ahl, P., et al., *Biochim. Biophys. Acta* (1997) 1329:370-382. Examples of negatively charged lipids obtained from natural sources which already contain non-zwitterionic moieties include phosphatidylglycerol and phosphatidylinositol obtained from egg and plant sources respectively.

Liposomes of the present invention may be prepared such that they are sensitive to elevations of the temperature in the surrounding environment. The temperature-sensitivity of such liposomes allows the release of compounds entrapped within the interior aqueous space of the liposome, and/or the release of compounds associated with the lipid bilayer, at a target site that is either heated (as in the clinical procedure of hyperthermia) or that is at an intrinsically higher temperature than the rest of the body (as in inflammation). Liposomes that allow release of compounds in a temperature dependent manner are termed "thermosensitive liposomes" and contain low levels of cholesterol. Liposomes of the present invention comprise a lipid possessing a gel-to-liquid crystalline transition temperature in the hyperthermic range (e.g., the range of from approximately 38° C. to approximately 45° C.). Preferred are phospholipids with a phase-transition temperature of from about 38° C. to about 45° C., and more preferred are phospholipids whose acyl groups are saturated. A particularly preferred phospholipid is dipalmitoylphosphatidylcholine (DPPC).

Thermosensitive liposomes of the present invention may incorporate a relatively-water soluble surface active agent, such as a lysolipid, into a bilayer composed primarily of a relatively water-insoluble molecule, such as a di-chain phospholipid (e.g., DPPC). Incorporation of the surface active agent in the gel phase of the primary lipid component enhances the release of contents from the resulting liposome when heated to the gel-liquid crystalline phase transition temperature of the primary lipid. Preferred surface active agents are lysolipids, and a particularly preferred surface active agent is monopalmitoylphosphatidylcholine (MPPC). Suitable surface-active agents are those that are compatible with the primary lipid of the bilayer, and that desorb when the lipid melts to the liquid phase. Additional suitable surface-active agents for use in phospholipid bilayers include palmitoyl alcohols, stearoyl alcohols, palmitoyl, stearoyl, glyceryl monopalmitate, glyceryl monooleate, and mono-acylated lipids such as sphingosine and sphingamine.

Liposomes of this invention may also be prepared such that the liquid crystalline transition temperature is greater than 45° C. In this case, vesicle-forming lipids making up the liposome are phospholipids such as PC or PE. The preferred phospholipid is PC. When selecting lipids, precautions should be taken since phase separation may occur if acyl chain lengths of these lipids differ by four or more methylene groups. Preferably the lipid will have two saturated fatty acids, the acyl chains of which being independently selected from the group consisting of stearoyl (18:0), nonadecanoyl (19:0), arachidoyl (20:0), heniecosanoyl (21:0), behenoyl (22:0), tricosanoyl (23:0), lingnoceroyl (24:0) and cerotoyl (26:0). Preferably, at least one (and more preferably both) of the acyl chains will be 18:0, or longer.

Embodiments of this invention may make use of liposomes having substantially no cholesterol having phase transition temperatures above that which would be useful for thermosensitive applications (e.g., about 45° C. or more) which exhibit enhanced drug retention as described in PCT/CA01/00655 published 15 Nov. 2001 (hereby incorporated by reference). Such liposomes include cholesterol-free liposomes having at least 60 mol % of phospholipids having at least one acyl chain of more than 18 carbon atoms.

Embodiments of this invention may make use of liposomes that are substantially free of cholesterol which provide increased systemic retention of agents when loaded according to the pH gradient loading technique with internal loading buffer concentrations below about 200 mM. Such liposomes are described in U.S. Ser. No. 60/331,249 filed 13 Nov. 2001, which is hereby incorporated by reference. Agents that demonstrate poor systemic retention in cholesterol-free liposomes may be more stably retained in accordance with this embodiment.

Embodiments of this invention may employ cholesterol-free liposomes which exhibit increased systemic retention of encapsulated therapeutic agents when the osmolarity of the internal buffer is selected to be near the osmolarity of a medium in which the liposomes are present when administered by injection. Such liposomes are described in U.S. Ser. No. 60/331,249 filed 13 Nov. 2001, which is hereby incorporated by reference. Thus, this embodiment includes the use of low solute containing cholesterol-free liposomes and injection media containing cholesterol-free liposomes in which the liposome internal buffer is matched to the solute osmolarity of the media.

Embodiments of this invention may make use of "thermosensitive" liposomes which destabilize at temperatures that can be applied to a patient (e.g., about 45° C. or less), including those described in U.S. Ser. No. 60/339,405 filed 14 Dec. 2001, which is hereby incorporated by reference. Thus, this embodiment may include or may result from the use of methods for delivering an agent to a site of interest in a subject by administering thermosensitive liposomes containing an active agent to a subject, allowing an extended time period for liposome localization to the site of interest, and subsequently administering hyperthermic treatment at the site of interest to cause the release of the liposome contents.

Embodiments of this invention may also make use of cholesterol-free liposomes which comprise hydrophilic moieties conjugated to lipids. Such liposomes are resistant to fusion and leakage of agent subsequent to freezing and are described in U.S. Ser. No. 60/331,248 filed 13 Nov. 2001, which is hereby incorporated by reference.

In one aspect of the invention, cholesterol-free liposomes are provided wherein the negatively charged lipid is incorporated in the liposome at greater than 10 mol %. In this aspect of the invention, the non-zwitterionic moiety is preferably a short-chain alcohol such as glycerol. Most preferably, the vesicle-forming lipids making up the liposome in this embodiment of the invention are selected such that the phase transition temperature of the liposome is greater than about 40° C. All other preferred features and conditions for this aspect of the invention are generally as described above.

Determination of the circulation longevity of a liposome may be carried out by means known in the art, including the methods described in the Examples below involving intravenous administration to a test animal and monitoring of blood levels. This determination may be made for a liposome intended for intravenous administration by formulating the liposome or lipid carrier in a suitable vehicle or diluent for intravenous administration, administering the formulation, and monitoring blood levels. The determination may be made by measuring the amount of a component such as a radioactive label present in a liposome or lipid carrier after administration to an animal model of disease.

Embodiments of this invention may make use of cholesterol-free liposomes which are selected or are made to behave comparably to cholesterol-containing liposomes through the incorporation of a hydrophilic moiety conjugated to a lipid such as is disclosed in U.S. Ser. No. 60/339,404 filed 14 Dec. 2001, which is hereby incorporated by reference. Such embodiments of the present invention may include, or may result from the use of methods of preparing or selecting liposomes using a testing format based on the comparison of circulation longevity of a cholesterol-free liposome having a phase transition temperature mildly hyperthermic to a subject's body temperature to circulation longevity of a comparable cholesterol-containing liposome. Such selected liposome compositions allow for increased liposome stability and drug retention properties.

The liposomes of the invention will be useful in delivering drugs and will thus be formulated to contain a biologically active agent.

A wide variety of agents may be encapsulated in the liposomes of the present invention. Liposomes of this invention may also be frozen with agent encapsulated or the agent may be encapsulated subsequent to the freezing. The term "agent" refers to chemical moieties that may be used in therapeutic and diagnostic applications. The terms "therapeutic agent" and "drug" as used herein refer to chemical moieties used in therapy and for which liposome-based drug delivery is desirable. The liposomes of this invention may be encapsulated with therapeutic agents such as anti-neoplastic agents, anti-viral agents and anti-microbial agents. The terms "anti-microbial agent" and "anti-viral agent" as used herein refers to chemical moieties having an effect on the growth, proliferation and survival of microbes and viruses respectively. Anti-microbial agents include, but are not limited to penicillin G, streptomycin, ampicillin, penicillin, carbenicillin, tetracycline, streptomycin, amphotericin B, vancomycin and floxacin and derivatives floxacin such as ciprofloxacin, norfloxacin, gatrifloxacin, levofloxacin, moxifloxacin and trovafloxacin. Anti-viral agents include AZT. The term "anti-neoplastic agent" as used herein refers to chemical moieties having an effect on the growth, proliferation, invasiveness or survival of neoplastic cells or tumours. Anti-neoplastic therapeutic agents include alkylating agents, antimetabolites, cytotoxic antibiotics and various plant alkaloids and their derivatives.

Agents may be encapsulated inside liposomes of the present invention by passive loading techniques known in the art. Passive methods of encapsulating therapeutic agents in liposomes involve encapsulating the agent during the synthesis of the liposomes. In this method, the agent may be membrane associated or encapsulated within an entrapped aqueous space. This includes a passive entrapment method described by Bangham, et al., *J. Mol. Biol.* (1965) 12:238 where the aqueous phase containing the agent of interest is put into contact with a film of dried vesicle-forming lipids deposited on the walls of a reaction vessel. Upon agitation by mechanical means, swelling of the lipids will occur and multilamellar vesicles (MLVs) will form. Using extrusion, the MLVs can be converted to large unilamellar vesicles (LUVs) or small unilamellar vesicles (SUVs) following sonication. Another method of passive loading that may be used includes that described by Deamer, et al., *Biochim. Biophys. Acta* (1976) 443:629. This method involves dissolving vesicle-forming lipids in ether and, instead of first evaporating the ether to form a thin film on a surface, this film being thereafter put into contact with an aqueous phase to be encapsulated, the ether solution is directly injected into said aqueous phase and the ether is evaporated afterwards, whereby liposomes with encapsulated agents are obtained. A further method that may be employed is the Reverse Phase Evaporation (REV) method described by Szoka, et al., *P.N.A.S.* (1978) 75:4194 in which a solution of lipids in a water insoluble organic solvent is emulsified in an aqueous carrier phase and the organic solvent is subsequently removed under reduced pressure.

Other methods of passive entrapment that may be used include subjecting liposomes to successive dehydration and rehydration treatment, or freezing and thawing. This technique is disclosed by Kirby, et al., *Biotechnology* (1984) 979-984. Also, Shew, et al., *Biochim. Biophys. Acta* (1985) 816:1-8 describe a method wherein liposomes prepared by sonication are mixed in aqueous solution with the solute to be encapsulated, and the mixture is dried under nitrogen in a rotating flask. Upon rehydration, large liposomes are produced in which a significant fraction of the solute has been encapsulated.

Agents may be encapsulated using active methods of encapsulation. Active loading involves the use of transmembrane gradients across the liposome membrane to induce uptake of a therapeutic agent after the liposome has been formed. This can involve a gradient of one or more ions including Na+, K+, H+, and/or a protonated nitrogen moiety. Active loading techniques that may be used in accordance with this invention include pH gradient loading, charge attraction, and drug shuttling by an agent that can bind to the drug.

Liposomes may be loaded according to the pH gradient loading technique. According to this technique, liposomes are formed which encapsulate an aqueous phase of a selected pH. Hydrated liposomes are placed in an aqueous environment of a different pH selected to remove or minimize a charge on the drug or other agent to be encapsulated. Once the drug moves inside the liposome, the pH of the interior results in a charged drug state, which prevents the drug from permeating the lipid bilayer, thereby entrapping the drug in the liposome.

To create a pH gradient, the original external medium is replaced by a new external medium having a different concentration of protons. The replacement of the external medium can be accomplished by various techniques, such as, by passing the lipid vesicle preparation through a gel filtration column, e.g., a Sephadex column, which has been equilibrated with the new medium (as set forth in the examples below), or by centrifugation, dialysis, or related techniques. The internal medium may be either acidic or basic with respect to the external medium.

After establishment of a pH gradient, a pH gradient loadable agent is added to the mixture and encapsulation of the agent in the liposome occurs as described above.

Loading using a pH gradient may be carried out according to methods described in U.S. Pat. Nos. 5,616,341, 5,736,155 and 5,785,987 incorporated herein by reference.

Therapeutic agents that may be loaded using pH gradient loading comprise one or more ionizable moieties such that the neutral form of the ionizable moiety allows the drug to cross the liposome membrane and conversion of the moiety to a charged form causes the drug to remain encapsulated within the liposome. Ionizable moieties may comprise, but are not limited to comprising, amine, carboxylic acid and hydroxyl groups. Agents that load in response to an acidic interior may comprise ionizable moieties that are charged in response to an acidic environment whereas drugs that load in response to a basic interior comprise moieties that are charged in response to a basic environment. In the case of an basic interior, ionizable moieties including but not limited to carboxylic acid or hydroxyl groups may be utilized. In the case of an acidic interior, ionizable moieties including but not limited to primary, secondary and tertiary amine groups may be used. Preferably, the pH gradient loadable agent is a therapeutic agent and most preferably an anti-neoplastic agent, antimicrobial agent or an anti-viral agent. Examples of therapeutic agents that can be loaded into liposomes by the pH gradient loading method and therefore may be used in this invention include, but are not limited to anthracycline antibiotics such as doxorubicin, daunorubicin, mitoxantrone, epirubicin, aclarubicin and idarubicin; anti-neoplastic antibiotics such as mitomycin, bleomycin and dactinomycin; vinca alkaloids such as vinblastine, vincristine and navelbine; purine derivatives such as 6-mercaptopurine and 6-thioguanine; purine and pyrimidine derivatives such as 5-fluorouracil; camptothecins such as topotecan, irinotecan, lurtotecan, 9-aminocamptothecin, 9-nitrocamptothecin and 10-hydroxycamptothecin; cytarabines such as cytosine arabinoside; antimicrobial agents such as ciprofloxacin and salts thereof. This invention is not to be limited to those drugs currently available, but extends to others not yet developed or commercially available, and which can be loaded using the transmembrane pH gradients.

Various methods may be employed to establish and maintain a pH gradient across a liposome. This may involve the use of ionophores that can insert into the liposome membrane and transport ions across membranes in exchange for protons (see, for example, U.S. Pat. No. 5,837,282). Buffers encapsulated in the interior of the liposome that are able to shuttle protons across the liposomal membrane and thus set up a pH gradient (see, for example, U.S. Pat. No. 5,837,282) may also be utilized. These buffers comprise an ionizable moiety that is neutral when deprotonated and charged when protonated. The neutral deprotonated form of the buffer (which is in equilibrium with the protonated form) is able to cross the liposome membrane and thus leave a proton behind in the interior of the liposome and thereby cause an increase in the pH of the interior. Examples of such buffers include methylammonium chloride, methylammonium sulfate, ethylenediammonium sulfate (see U.S. Pat. No. 5,785,987) and ammonium sulfate. Internal loading buffers that are able to establish a basic internal pH, can also be utilized. In this case, the neutral form of the buffer is protonated such that protons are shuttled out of the liposome interior to establish a basic interior. An example of such a buffer is calcium acetate (see U.S. Pat. No. 5,939,096).

Charge attraction methods may be utilized to actively load therapeutic agents. Charge attraction mechanisms for drug loading involves creating a transmembrane potential across the membrane by creating a concentration gradient for one or more charged species. Thus, for a drug that is negatively charged when ionized, a transmembrane potential is created across the membrane that has an inside potential which is positive relative to the outside potential. For a drug that is positively charged, the opposite transmembrane potential would be used.

In one embodiment, subsequent to preparation, the liposomes are subjected to temperatures below 0° C. such that they are present in the frozen state. The liposomes may be frozen by: immersion in liquid nitrogen, dry ice, a −20° C. conventional freezer or a −80° C. or −70° C. conventional freezer. In alternative examples, the liposomes may be frozen in liquid nitrogen followed by immersion in a freezer. Liposomes can be stably stored in the frozen state for extended periods of time until they are to be used. Subsequent to freezing, the liposomes may be are thawed for further use, by subjection to temperatures above 0° C.

The liposomes may comprise encapsulated agents prior to subjection to temperatures below 0° C. This may involve loading the agent into preformed liposomes using aforementioned active and passive loading techniques. If the encapsulated agent is a therapeutic agent, the thawed liposomes may be used directly in therapy following known procedures for administering liposome encapsulated agents.

The liposomes may be actively loaded with agent subsequent to freezing. This allows frozen liposomes to be provided to drug manufacturers in an unencapsulated form which the manufacturers can subsequently actively load with agent. A preferred active loading method is the pH gradient loading method described above. Liposomes may be frozen with a pH gradient across the membrane or the gradient may be generated subsequent to freezing.

In the case where the gradient is generated subsequent to freezing, the external buffer may be exchanged and replaced by a new external medium having a different concentration of protons. The external pH may also be adjusted by addition of an acid or a base. The replacement of the external medium can be accomplished by various techniques, such as, by passing the lipid vesicle preparation through a gel filtration column, e.g., a Sephadex column, which has been equilibrated with the new medium (as set forth in the examples below), or by centrifugation, dialysis, or related techniques. The internal medium may be either acidic or basic with respect to the external medium.

Liposomes of the present invention may also be subjected to more than one cycle of freezing and thawing.

Following freezing, the liposome preparation may be dehydrated by removal of the aqueous solvent that the liposomes are immersed in. The liposomes are preferably dehydrated using standard freeze-drying equipment or equivalent apparatus; that is, they are preferably dehydrated under reduced pressure. Prior to use, the dried liposome preparation may be reconstituted by the addition of an appropriate solvent that the liposomes are to be suspended in. Preferably, the liposome preparation is dehydrated by the introduction of reduced pressure. Means to apply reduced pressure include the use of vacuum pumps or equivalent apparatus. The dehydration process is preferably carried out at reduced temperatures rather than at room temperature. Once the liposomes have been dehydrated, they can be stored for extended periods of time until they are to be used.

The term "cryostable" in this specification refers to liposomes that are substantially resistant to any one of several undesirable effects that occur upon the exposure of the liposome composition to a temperature below about 0° C. sufficient to cause one of the undesirable effects. Undesirable effects include, but are not limited to, an increase in the liposome size, size distribution or turbidity of the liposome preparation due to aggregation and/or fusion of the liposomes, and loss of encapsulated agent. Typically, undesirable side effects occur at a temperature below 0° C., more typically below −5° C. and even more typically below −10° C.

Whether or not a liposome is cryostable may be assessed, for example, by measuring undesirable effects associated with exposure of the liposomes to temperatures below 0° C. Measurement of the change in size of the liposomes before and after subjection to temperatures below 0° C. may be carried out as described below using quasi-elastic light scattering (QELS). Fusion of the liposomes may also be measured by other means including fluorescence resonance energy transfer. This involves measurement of energy transfer from an excited probe to a second probe due to close proximity of the two probes. Measurement of the release of an encapsulated agent subsequent to freezing, may be carried out as disclosed below. Encapsulated agent may be incorporated into the liposomes using active or passive loading methods described above. Leakage of entrapped agent may be measured by determination of the amount of agent entrapped prior to and subsequent to freezing. The agent may be quantified by scintillation counting in the case of radiolabeled agent or by spectroscopy in the case of an agent that comprises a detectable absorbance for quantification. Alternatively, the agent may be quantified by gas chromatography, high performance liquid chromatography, atomic absorption and related techniques.

Liposome preparations may also be visually inspected for macroscopic evidence of freezing damage, such as the presence of macroscopic particles, and for clarity of the suspension or turbidity in comparison to unfrozen control samples. Turbidity may be measured using a spectrophotometer set at 650 nm. The liposomes may also be tested for large particles, aggregates or other changes that might indicate that the liposome is not cryostable by centrifugation. Subsequent to centrifugation, the centrifuge tube is observed for the presence of particles at the bottom of the tube that can be seen with the naked eye.

The undesirable effects associated with the exposure of the liposomes to temperatures below 0° C. may be compared to equivalent liposome formulations containing cholesterol.

This invention also includes methods of administering liposomes of this invention to a mammal, and methods of treating a mammal affected by or susceptible to or suspected of being affected by a disorder (e.g., cancer). Examples of medical uses of the compositions of the present invention include but are not limited to treating cancer, treating cardiovascular diseases such as hypertension, cardiac arrhythmia and restenosis, treating bacterial, fungal or parasitic infections, treating and/or preventing diseases through the use of the compositions of the present inventions as vaccines, treating inflammation or treating autoimmune diseases. In particular, the invention encompasses a method of administering a liposome to a subject, comprising administering a pharmaceutical composition comprising liposomes of the invention. Methods of treatment or of administration will generally be understood to comprise administering the pharmaceutical composition at a dosage sufficient to ameliorate said disorder or symptoms thereof.

For treatment of human ailments, a qualified physician may be expected to determine how the compositions of the present invention should be utilized with respect to dose, schedule and route of administration using established protocols. Such applications may also utilize dose escalation should active agents encapsulated in delivery vehicle compositions of the present invention exhibit reduced toxicity to healthy tissues of the subject.

Pharmaceutical compositions comprising the liposomes of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, 5% dextrose and the like, including glycoproteins for enhanced stability, such as albumin, lipoprotein, globulin, etc. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of liposomes, in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. Alternatively, liposomes composed of irritating lipids may be diluted to low concentrations to lessen inflammation at the site of administration. For diagnosis, the amount of liposomes administered will depend upon the particular label used, the disease state being diagnosed and the judgement of the clinician.

Preferably, the pharmaceutical compositions are administered parenterally, i.e., intraarterialy, intravenously, intraperitoneally, subcutaneously, or intramuscularly or via aerosol. Aerosol administration methods include intranasal and pulmonary administration. More preferably, the pharmaceutical compositions are administered intravenously or intraperitoneally by a bolus injection. For example, see Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578. Particular formulations which are suitable for this use are found in Remington's Pharmaceutical Sciences, Mack Publishing Company, Philadelphia, Pa., 17th ed. (1985).

The following examples are offered to illustrate but not to limit the invention.

PREPARATION A

Methods for Preparation of Large Unilamellar Liposomes

Lipids were dissolved in chloroform solution and subsequently dried under a stream of nitrogen gas and placed in a vacuum pump to remove solvent. Trace levels of radioactive lipid $^3$H-CHE or $^{14}$C-CHE were added to quantify lipid during the formulation process and following intravenous administration. The resulting lipid film was placed under high vacuum for a minimum of 2 hours. The lipid film was hydrated in the solution indicated to form multilamellar vesicles (MLVs). The resulting preparation was extruded 10 times through stacked polycarbonate filters with an extrusion apparatus (Lipex Biomembranes, Vancouver, BC) to achieve a mean liposome size between 80 and 150 nm. All constituent lipids of liposomes are reported in mole %.

PREPARATION B

Methods for Quantification of Drug Loading

At various time points after initiation of drug loading, aliquots were removed and passed through a Sephadex G-50 spin column to separate free from encapsulated drug. Lipid levels were determined by liquid scintillation counting. Where employed, levels of radiolabeled daunorubicin ($^3$H-daunorubicin) and FUDR ($^3$H-FUDR) present in the eluant were measured by liquid scintillation counting. Irinotecan levels were measured by absorbance at 370 nm against a standard curve of free drug. To a specified volume of eluant, Triton X-100 was added to solubilize the irinotecan-containing liposomes. Following addition of detergent, the mixture was heated to 100° C. and allowed to cool to room temperature before measurement of the absorbance.

EXAMPLE 1

The Blood Stability of DSPC Liposomes Increases with Increasing Phosphatidylglycerol (PG) Content The ability of different levels of phosphatidylglycerol (PG) to extend the blood residence time and to enhance the drug retention properties of liposomes containing distearoylphosphatidylcholine (DSPC) as the bulk lipid component was investigated. DSPC liposomes were prepared with varying levels of distearoylphosphatidylglycerol (DSPG) and loaded with daunorubicin in response to encapsulated $CuSO_4$. The plasma lipid levels and drug concentrations were determined after administration to mice.

DSPC liposomes containing DSPG at 10, 20 and 30 mole % were prepared as described in the methods by dissolving DSPC in chloroform and DSPG lipids in chloroform/methanol/water (16:8:1 v/v) and combining the preparations at mole ratios of 90:10, 80:20 and 70:30 along with the radioactive marker $^{14}$C-CHE. Lipid films were left under vacuum overnight to remove any residual solvent followed by rehydration in 150 mM $CuSO_4$, 20 mM histidine, pH 7.4. The liposomes were then buffer exchanged into saline to remove external copper and further exchanged into 300 mM sucrose, 20 mM HEPES, 5 mM EDTA (SHE buffer), pH 7.4 using a hand-held tangential flow dialysis column.

The uptake of daunorubicin (containing trace levels of $^3$H-daunorubicin) into the DSPC/DSPG liposomes was established by incubation of the liposomes with drug at a drug-to-lipid weight ratio of 0.1. Complete drug loading, measured by spin column analysis as described in the methods, was achieved after incubation of the solution at 60° C. The external buffer was exchanged for saline using a hand-held tangential flow column. The resulting daunorubicin loaded DSPC/DSPG liposomes were injected into Balb/c mice (3 mice per time point) at a lipid dose of 100 mg/kg and a drug dose of 10 mg/kg. At the indicated time points, blood was collected by cardiac puncture and placed into EDTA coated microtainers. The samples were centrifuged and plasma was carefully transferred to another tube. Recovery of lipid and drug was monitored by dual labeled scintillation counting. Data points represent the average results, +/− standard deviation (SD).

Figure 1A:
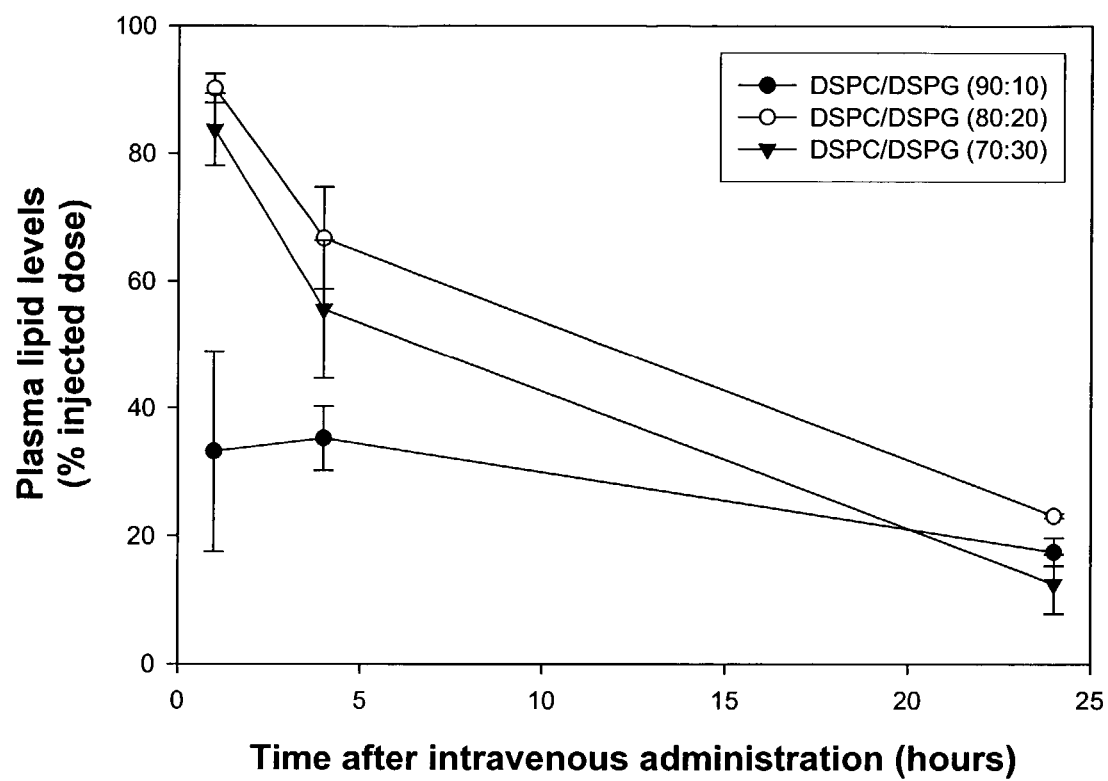
FIG. 1A is a graph showing the percent injected lipid remaining in the blood after intravenous administration of daunorubicin-loaded liposomes containing DSPC/DSPG at mole ratios of 90:10 (filled circles), 80:20 (open circles) and 70:30 (inverted triangles).

The results demonstrate that optimal blood residence of the liposomes was achieved by the incorporation of 20 mole % DSPG (FIG. 1A). In contrast, Mehta et. al. in WO99/59547 reported that DPPC/Chol liposomes prepared with less than 15 mole % DMPG displayed extended blood half-lives relative to liposomes prepared with 20 mole % DMPG. Liposomes in these previous studies utilized a bulk lipid (DPPC) having a phase transition temperature below that employed in the present invention and cholesterol (Chol) as a stabilizing lipid. Thus, these results demonstrate that the nature of the lipid components making up phosphatidylglycerol containing liposomes can affect the plasma stability properties of the carrier.

Figure 1B:
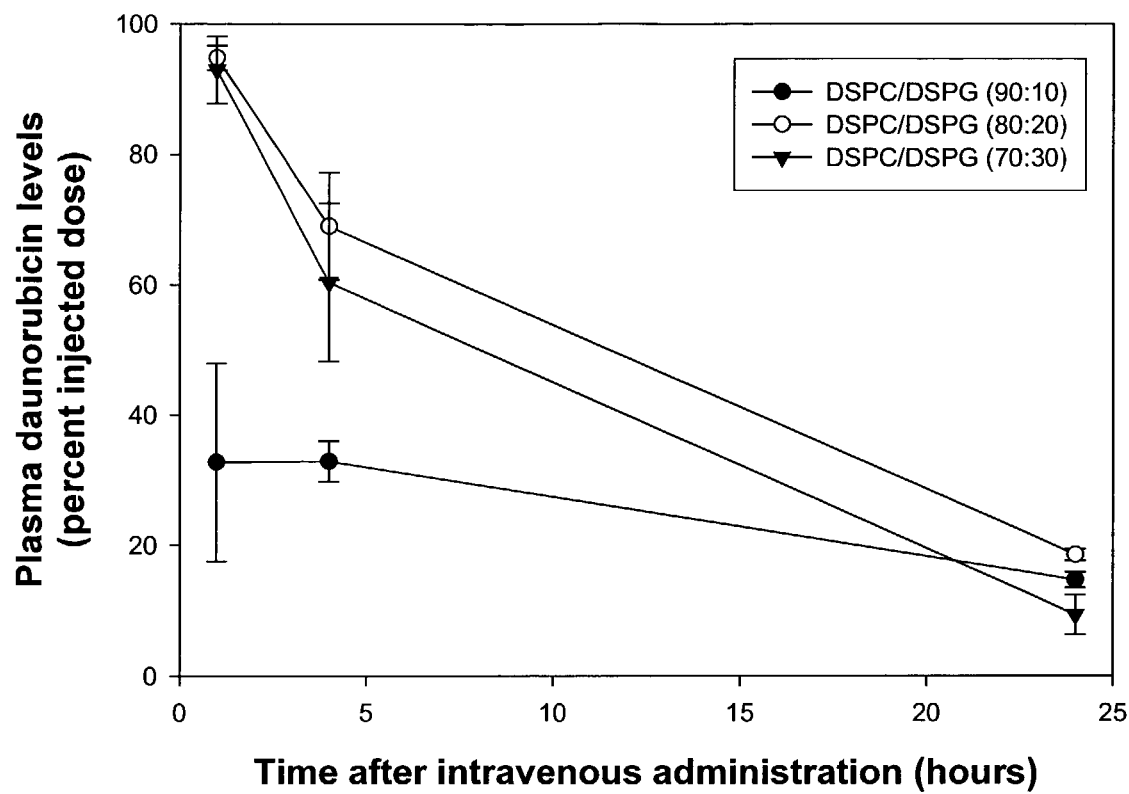
FIG. 1B is a graph showing the percent injected daunorubicin remaining in the blood after intravenous administration of daunorubicin-loaded liposomes containing DSPC/DSPG at mole ratios of 90:10 (filled circles), 80:20 (open circles) and 70:30 (inverted triangles).

Previously, it has been demonstrated that liposomes prepared with hydrophilic polymers such as polyethylene glycol and lipids such as $GM_1$ have the ability to extend the circulation lifetime of liposomes. These results illustrate that the polymer, poly(ethylene glycol) (PEG), is not required for plasma stability and that non-zwitterionic moieties such as glycerol attached to the head group can engender long circulating properties to liposomes. Although not wishing to be bound by theory, the presence of the hydroxyl groups on the PG head group may facilitate hydrogen bonding with water molecules in the external medium creating a hydration shell surrounding the liposome Results depicted in FIG. 1B indicate that plasma blood levels of daunorubicin also increased with increasing levels of DSPG. This data thus demonstrates that in addition to decreasing the elimination of liposomes from the blood compartment, the DSPG containing liposomes exhibit excellent drug retention properties in vivo.

EXAMPLE 2

Retention of 5-Fluoro-2'-Deoxyuridine (FUDR) Is Optimal when Encapsulated in Cholesterol-Free, PG-Containing Liposomes The effect of the incorporation of cholesterol (Chol) in liposomal formulations on the in vivo retention of passively entrapped 5-fluoro-2'-deoxyuridine (FUDR) was examined and compared to the retention properties of FUDR encapsulated in liposomes containing phosphatidylglycerol. This was carried out by passively entrapping FUDR in liposomes consisting of DSPC/Chol (55:45 mole ratio) and DSPC/DSPG (80:20 mole ratio) and comparing the drug-to-lipid ratios after administration of the formulations to mice. DSPC/Chol liposomes were selected as a control for these studies as this formulation has historically been utilized in the art because of its ability to optimally retain drug in part due to the stabilizing effect of cholesterol. DSPG was incorporated into DSPC liposomes at 20 mole % as this level of PG was found to confer to the liposomes optimal circulation longevity as demonstrated in Example 1.

DSPC/Chol and DSPC/DSPG lipid films labeled with $^{14}$C-CHE were prepared as described in Example 1 and hydrated in a solution consisting of FUDR in HBS, pH 7.4 containing trace levels of $^3$H-FUDR. Subsequent to extrusion, the liposomes were buffer exchanged into normal saline through the use of tangential flow dialysis. The FUDR loaded liposomes were administered to Balb/c mice (3 mice per time point) at a FUDR dose of 20 μmole/kg with a resulting lipid dose of 200 μmole/kg. At the indicated time points, blood was collected by cardiac puncture and placed into EDTA coated microtainers. The samples were centrifuged and plasma was carefully transferred to another tube. Lipid recovery and plasma drug concentrations were determined by liquid scintillation counting. Data points are the mean of +/− SD from 3 points.

Figure 2:
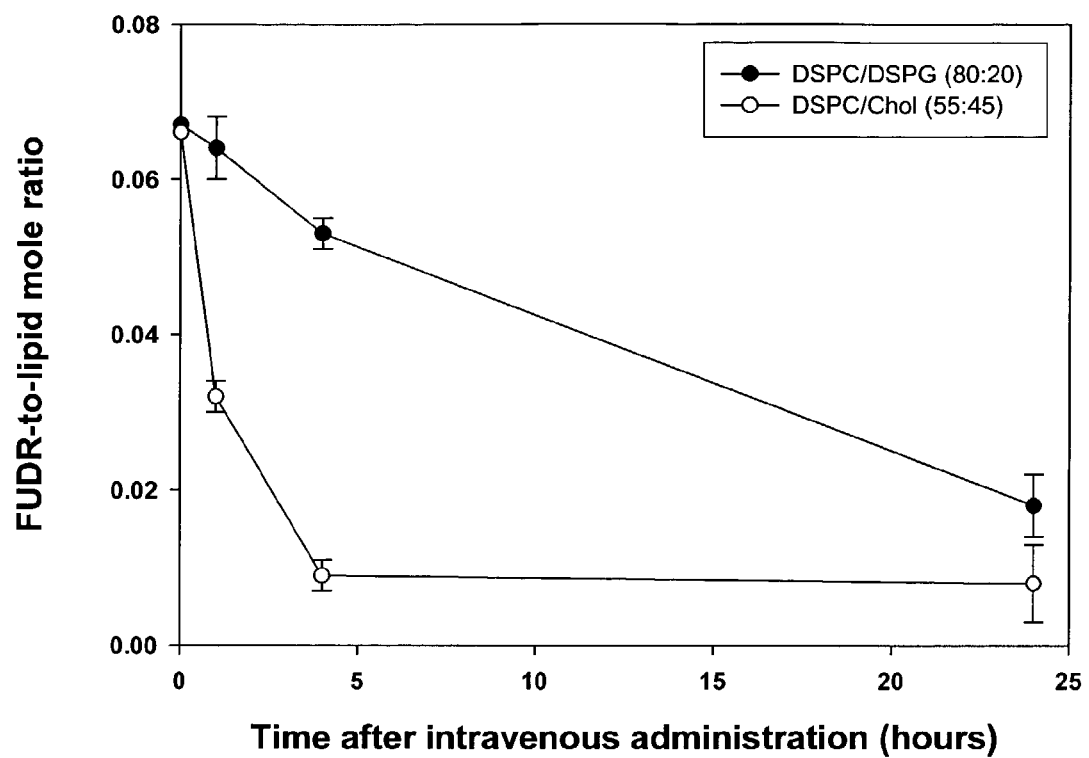
FIG. 2 is a graph showing the FUDR-to-lipid ratio at various time points after intravenous administration of DSPC/DSPG (80:20 mole ratio) and DSPC/Chol (55:45 mole ratio) liposomes passively entrapped with FUDR.

Results in FIG. 2 demonstrate that FUDR was optimally retained in DSPC/DSPG (80:20 mole ratio) formulations in relation to DSPC/Chol (55:45 mole ratio) formulations. These results suggest that enhanced FUDR retention is realized when PG is employed as a stabilizing lipid as a replacement for cholesterol.

EXAMPLE 3

Decrease in Cholesterol Content Results in Increased Retention of FUDR in PG-Containing Liposomes Containing Irinotecan The effect of cholesterol on the retention of passively entrapped FUDR in PG containing liposomes subsequently loaded with irinotecan was investigated in order to examine the effect of cholesterol on the retention of FUDR in a formulation containing two encapsulated drugs. The inventors have previously demonstrated that a synergistic interaction of two drugs in vivo optimally occurs if the release rates of the two drugs are comparable. Retention of drug can be adjusted by controlling parameters such as the acyl chain length of constituent lipids, the cholesterol content and the osmolarity of the internal compartment of the liposome. These studies were conducted in order to explore the ability of cholesterol to modulate the release rate of one drug in a dual loaded liposome with the ultimate goal of achieving coordinated release of both drugs. In order to determine the effect of increasing levels of cholesterol on the retention of passively entrapped FUDR, DSPG containing liposomes were prepared with 5, 10, 15 and 20 mol % cholesterol and the plasma drug-to-lipid ratios were measured after intravenous administration to mice. As in the previous example, PG was incorporated in the liposomes at 20 mole % as this level of PG has been found to optimally confer long-circulating properties to DSPC liposomes.

Lipid films consisting of DSPC/Chol/DSPG with cholesterol incorporated at 5, 10, 15 and 20 mole % and with PG held constant at 20 mole % were prepared as described in Example 1 by dissolving DSPC and cholesterol in chloroform and DSPG in chloroform/methanol/water and combining the preparations at the appropriate mole ratios. After removal of solvent, the lipid films were redissolved in chloroform and dried down once again followed by hydration in a solution consisting of 250 mM $CuSO_4$ containing 25 mg/mL FUDR with trace levels of $^3$H-FUDR. After extrusion, the liposomes were buffer exchanged into 300 mM sucrose, 20 HEPES, 30 mM EDTA, pH 7.4 using a hand-held tangential flow dialysis column. Subsequent to buffer exchange, the samples were loaded with irinotecan at 50° C. at a drug-to-lipid mole ratio of 0.1:1 and exchanged into HBS, pH 7.4 using a hand-held tangential flow column. The resulting dual loaded liposomes were administered to Balb/c mice at 340 μmole lipid/kg, 34 μmole FUDR/kg and 34 μmole irinotecan/kg. Blood was recovered at the indicated time points by cardiac puncture and placed into EDTA-coated microtainers; three mice were used for each time point (as in the previous examples, data points are the mean +/− the SD). The samples were centrifuged and plasma was carefully transferred to another tube. Lipid and FUDR concentrations were determined by liquid scintillation counting, and irinotecan concentrations were determined by HPLC analysis.

Figure 3:
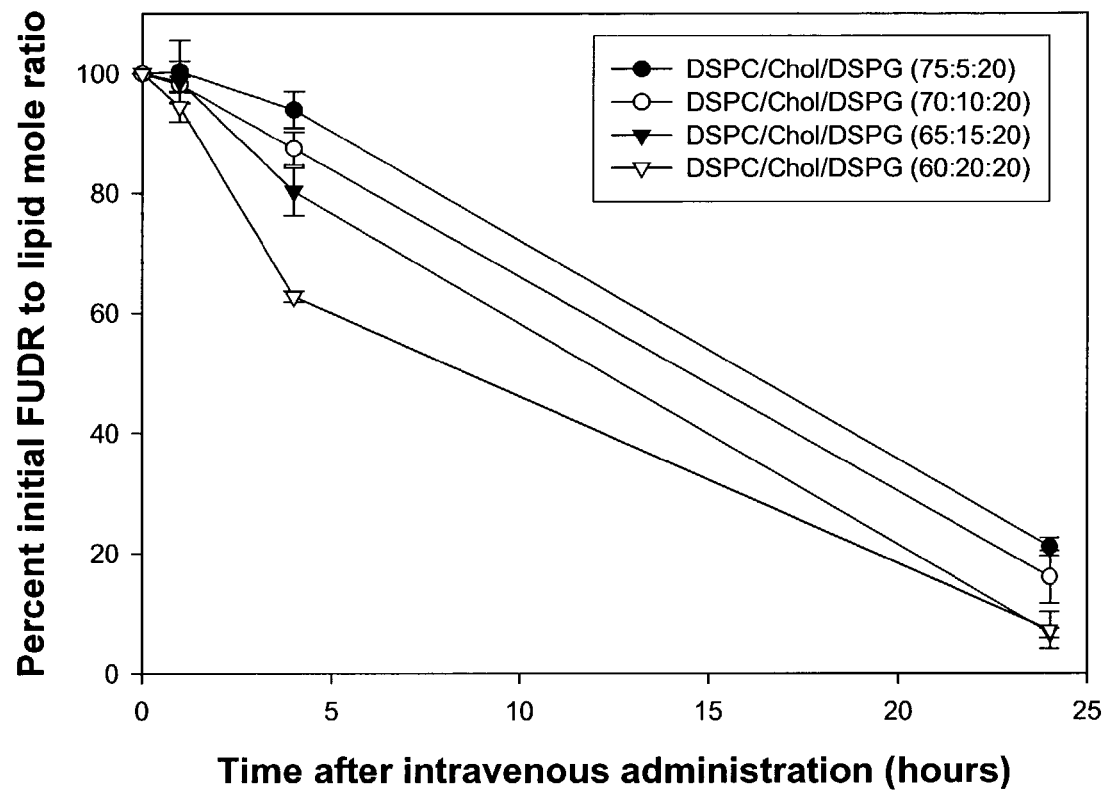
FIG. 3 is a graph showing the effect of cholesterol content on the percent initial FUDR-to-lipid ratio at various time points after intravenous administration of DSPC/DSPG liposomes co-loaded with FUDR and irinotecan. The liposomes contained cholesterol at 5 mole %.(filled circles), 10 mole % (open circles), 15 mole % (inverted, filled triangles) and 20 mole % (open, inverted triangles) and DSPG levels were held constant at 20 mole %.

Results in FIG. 3 demonstrate that as the cholesterol content in DSPC liposomes containing 20 mol % DSPG is increased, there is a concomitant decrease in the percent initial FUDR-to-lipid ratio. These results thus demonstrate that cholesterol can be employed to control the release kinetics of drug from PG-containing liposomes loaded with a second drug.

EXAMPLE 4

Blood Stability of Liposomes can Be Enhanced by Incorporation of Dipalmitoylphosphatidylglycerol (DPPG) and Phosphatidylinositol (PI)

The plasma residence time of DSPC liposomes containing dipalmitoylphosphatidylglycerol (DPPG) and phosphatidylinositol (PI) was examined in order to determine whether these lipids would also impart long circulating properties to these liposomes similar to that observed for DSPG. DSPG and DPPG both contain a glycerol head-group, but differ in that the acyl chain of DSPG contains 18 saturated carbon atoms while the acyl chains of DPPG contain only 16 saturated carbon atoms. PG and PI share common chemical characteristics in that both contain a negatively charged phosphate group shielded by a hydrophilic neutral moiety.

DPPG liposomes containing 10, 20 and 30 mole % DPPG were prepared as set forth in Example 1, except DPPG lipids were dissolved in chloroform/methanol (94:6 v/v) and $^3$H-CHE was employed as the lipid label. The resulting lipid films were hydrated in HBS, pH 7.4 and after extrusion the liposomes were injected into Balb/c mice (3 mice per time point) at a lipid dose of 100 mg/kg. At the indicated time points, blood was collected by cardiac puncture and placed into EDTA coated microtainers. The samples were centrifuged and plasma was carefully transferred to another tube. Recovery of lipid was monitored by liquid scintillation counting and data points represent the average results +/− SD.

Figure 4:
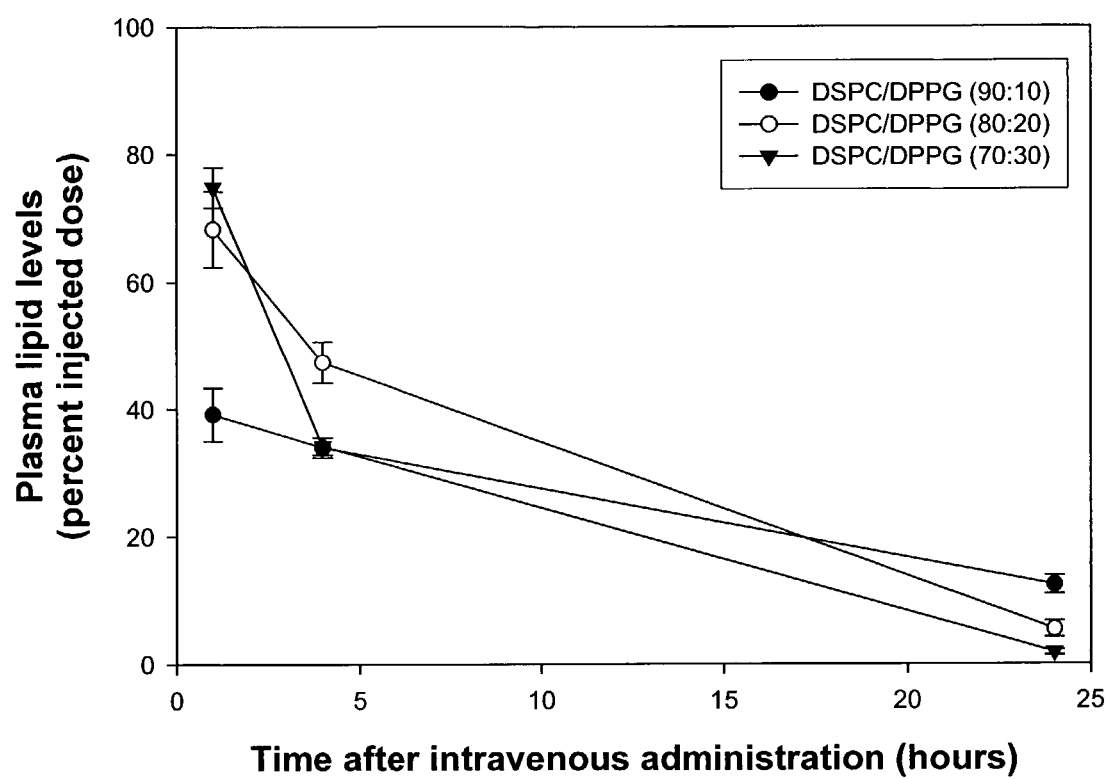
FIG. 4 is a graph showing the percent injected lipid remaining in the blood after intravenous administration of liposomes containing DSPC/DPPG at mole ratios of 90:10 (filled circles), 80:20 (open circles) and 70:30 (inverted circles).

DSPC/PI liposomes were prepared by dissolving DSPC lipids in chloroform and hydrogenated plant PI in chloroform/methanol/water (8:4:1 v/v). The lipids were then combined together at DSPC to PI mole ratios of 90:10, 80:20 and 70:30 with an appropriate amount of $^3$H-CHE. Chloroform was removed under a stream of $N_2$ gas while the temperature was maintained at 70° C. until very little solvent remained. The resulting lipid films were put under vacuum to remove the bulk of the solvent. The films were redissolved in a solution of chloroform containing methanol followed by removal of the solvent as indicated above. The lipid films were placed in a vacuum pump overnight to remove the remainder of the solvent followed by rehydration in HBS, pH 7.4. After extrusion, the resulting LUVs were injected into mice Balb/c mice (3 mice per time point) at a lipid dose of 100 mg/kg. At the indicated time points, blood was collected by cardiac puncture and placed into EDTA coated microtainers. The samples were centrifuged and plasma was carefully transferred to another tube. Recovery of lipid was monitored by liquid scintillation counting and data points represent the average results +/− standard deviation Results summarized in FIG. 4 indicate DPPG lipids impart long circulating properties to DSPC liposomes. Thus decreasing the length of the acyl chain component of the PG lipid by the removal of two methylene groups does not appear to substantially influence the ability of these lipids to confer long circulating properties to liposomes.

Figure 5:
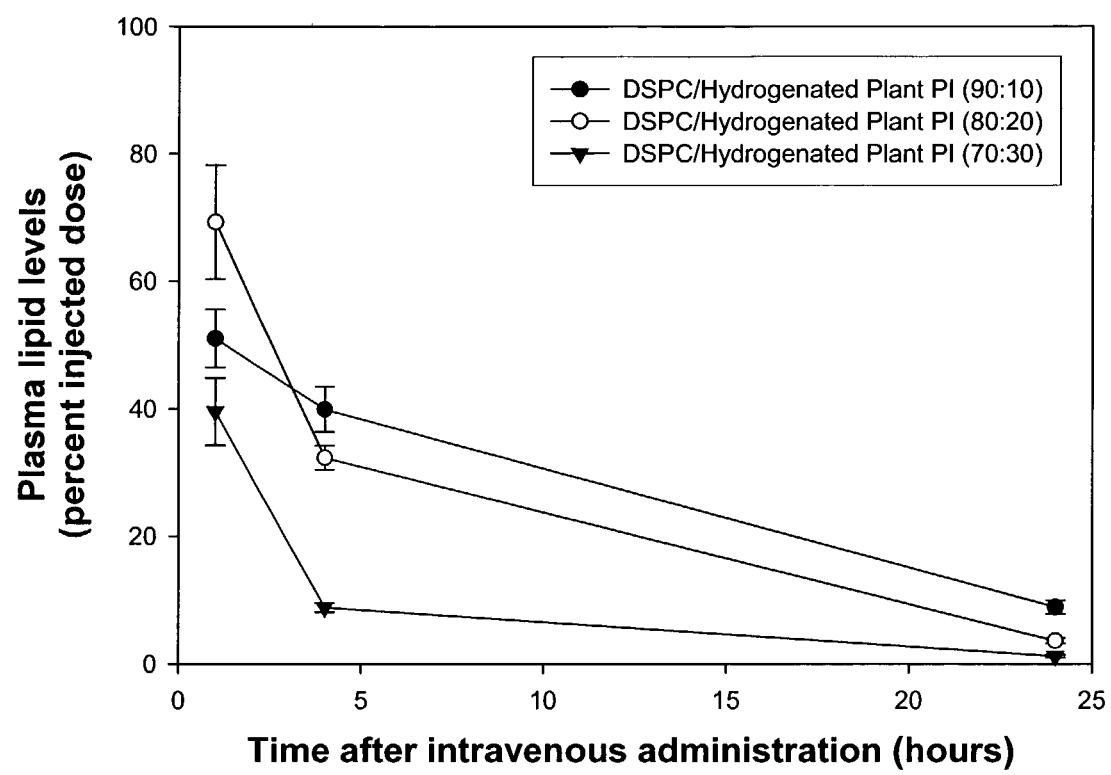
FIG. 5 is a graph showing percent injected lipid remaining in the blood after intravenous administration of liposomes containing DSPC/PI (hydrogenated plant) at molar ratios of 90:10 (filled circles), 80:20 (open circles) and 70:30 (inverted triangles).

Results shown in FIG. 5 demonstrate that similar to PG containing liposomes, formulations prepared with PI display extended circulation lifetimes. The inositol head group of PI thus appears to act in the same manner as a glycerol head group of PG to enhance the plasma stability of the liposomes.

EXAMPLE 5

Phosphatidylglycerol Liposomes Containing Low Levels of Cholesterol Resist the Detrimental Effects of Freezing It is preferable that liposome preparations exhibit extended chemical and physical stability properties in order for these compositions to be of practical use. This often requires the use of frozen or freeze-dried (lyophilized) product formats in order to avoid breakdown of labile drug and/or lipid components. Without the use of cryoprotectants, liposomes are generally prone to mechanical rupture, aggregation and fusion during the thawing/rehydration process. In order to examine whether phosphatidylglycerol containing liposomes co-loaded with FUDR and irinotecan and prepared with cholesterol at below 20 mole % were resistant to the detriment effects of freezing, DSPC liposomes were prepared with 0, 5, 10, 15 and 20 mole % cholesterol and subjected to temperatures of −20° C. and −70° C. Liposome size was measured before and after freezing and before and after loading of drug in order to measure the degree of liposome aggregation induced by loading of drug and thawing after freezing.

Lipid films with 0-20 mole % cholesterol, DSPG and DSPC and trace levels of $^{14}$C-CHE as were prepared as described in the methods. The lipid films were rehydrated in 250 mM CuSO$_4$ containing 100 mM FUDR with trace levels of $^3$H-FUDR. After extrusion, the liposomes were buffer exchanged into saline and then into 300 mM sucrose, 20 mM HEPES, 30 mM EDTA, (SHE buffer) pH 7.4 using a hand-held tangential flow column. This sample was then exchanged into 300 mM sucrose, 20 mM HEPES, pH 7.4 to remove any EDTA in the exterior buffer. The liposomes were loaded with irinotecan by incubating the liposomes with the drug at 50° C. for 5 minutes at a 0.1:1 drug-to-lipid mole ratio. The free drug was removed from the samples with buffer exchange into HBS using tangential flow. The samples were sized before and after drug loading using a NICOMP particle sizer. For freezing studies, the samples were frozen at –20° C. and –70° C. for 24 hours. After freezing, the samples were thawed to room temperature and an aliquot of the sample was then run down a Sephadex G-50 spun column and then centrifuged. The drug to lipid mole ratio for the spun column eluant was generated using liquid scintillation counting to determine lipid and 5-FUDR concentrations and absorbance at 370 nm against a standard curve to determine irinotecan concentrations. Particle sizing of the eluted liposomes was also determined using quasi-elastic light scattering. Standard deviation values for liposome size measurements ranged from 24% to 34% for liposomes prior to freezing, from 31% to 61% after freezing at –20° C. and from 32% to 47% for freezing at –70° C. All Chi squared values were less than 1.

Figure 6A:
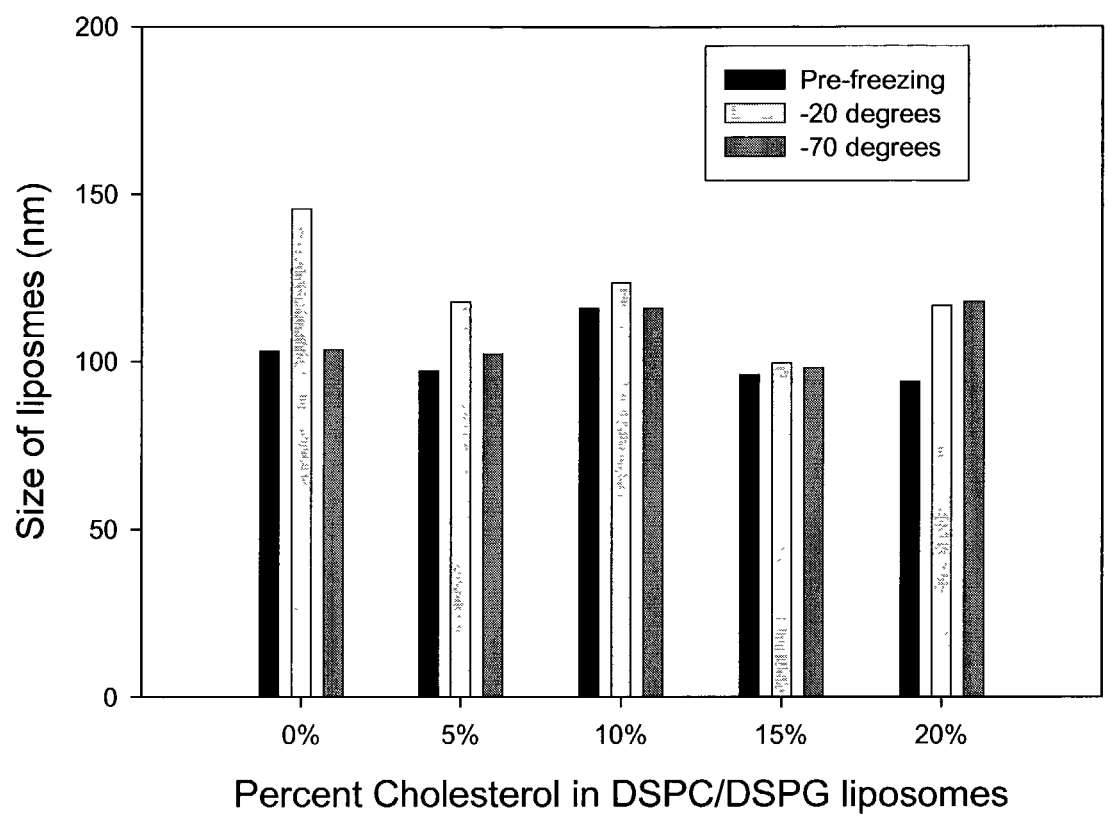
FIG. 6A is a histogram showing the size of DSPC/DSPG (80:20 mole ratio) liposomes co-loaded with FUDR and irinotecan before freezing after loading of both drugs, after freezing at −20° C. for 24 hours followed by thawing to room temperature and after freezing at −70° C. for 24 hours followed by thawing to room temperature.
Figure 6B:
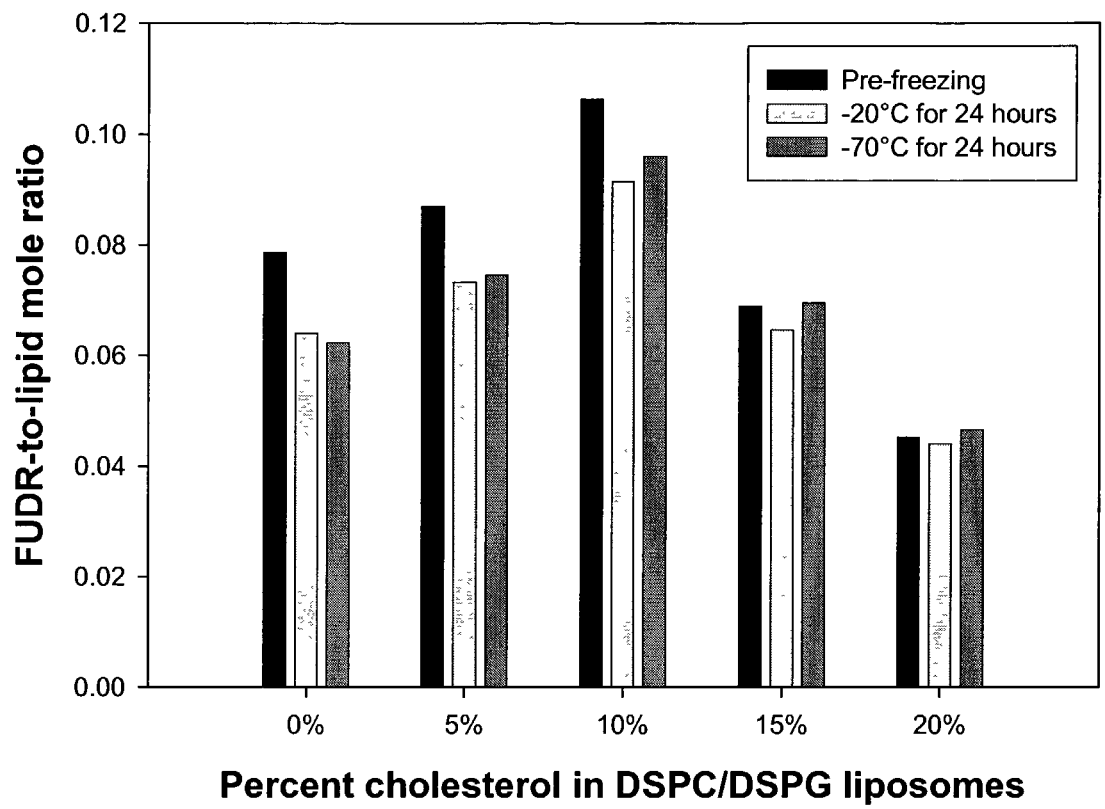
FIG. 6B is a histogram showing the FUDR-to-lipid ratio of DSPC/DSPG (80:20 mole ratio) liposomes co-loaded with FUDR and irinotecan before freezing after loading of both drugs, after freezing at −20° C. for 24 hours followed by thawing to room temperature and after freezing at −70° C. for 24 hours followed by thawing to room temperature.
Figure 6C:
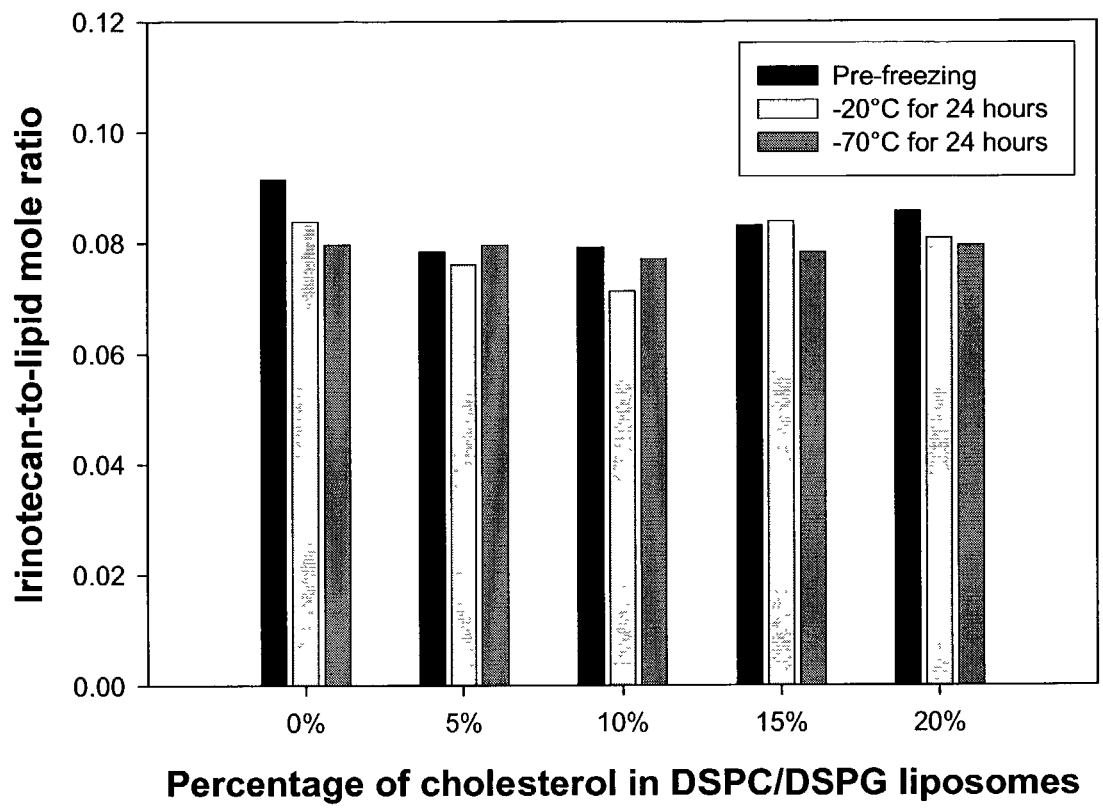
FIG. 6C is a histogram showing irinotecan-to-lipid ratio of DSPC/DSPG liposomes (80:20 mole ratio) co-loaded with FUDR and irinotecan before freezing after loading of both drugs, after freezing at −20° C. for 24 hours followed by thawing to room temperature and after freezing at −70° C. for 24 hours followed by thawing to room temperature.

Results summarized in FIG. 6A show that liposomes co-encapsulated with FUDR and irinotecan display optimal stability after freeze-thaw at –70° C. as evidenced by the observation that the liposome size did not change substantially prior to and subsequent to freezing. Examination of the retention of FUDR and irinotecan in the dual loaded liposomes before and after freezing at –20 and –70° C. revealed that FUDR was well-retained throughout the freeze/thaw process (FIG. 6B). Similar findings were observed for retention of irinotecan before and after freezing at –20 and –70° C. (FIG. 6C). Cumulatively, these results demonstrate that stabilizing lipids such as phosphatidylglycerol may be employed to protect liposomes against the detrimental effects of freezing without requiring the presence of cryoprotectants.

EXAMPLE 6

Cholesterol-Free Liposomes Prepared in the Absence of a pH Gradient Resist Aggregation Subsequent to Freezing Lipids were prepared in chloroform and subsequently dried under a stream of nitrogen gas and placed in a vacuum pump overnight. The samples were then hydrated with 300 mM citrate buffer pH 4.0, or HEPES buffered saline (HBS) pH 7.4 and passed through an extrusion apparatus (Lipex Biomembranes, Vancouver, BC) 10 times with 80 and 100 nm polycarbonate filters. Average liposome size was determined by quasi-elastic light scattering (QELS) using a NICOMP 370 submicron particle sizer at a wavelength of 632.8 nm. The liposomes were frozen in liquid nitrogen (–196° C.) for 24 hrs, allowed to thaw at room temperature followed by determination of average liposome size using a NICOMP particle sizer.

Figure 7:
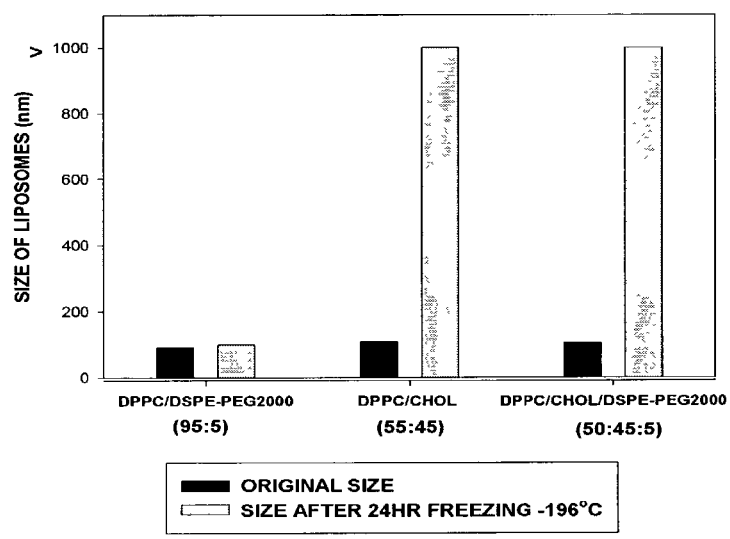
FIG. 7 is a histogram showing the size of liposomes containing 300 mM citrate buffer both inside and outside the liposomal membrane prior to (black bar) and subsequent to (grey bar) 24 hour freezing. Liposomes consisting of DPPC/DSPE-PEG2000 (95:5 mol %), DPPC/cholesterol (55:45 mol %) and DPPC/cholesterol/DSPE-PEG2000 (50:45:5 mol %) were tested.
Figure 8:
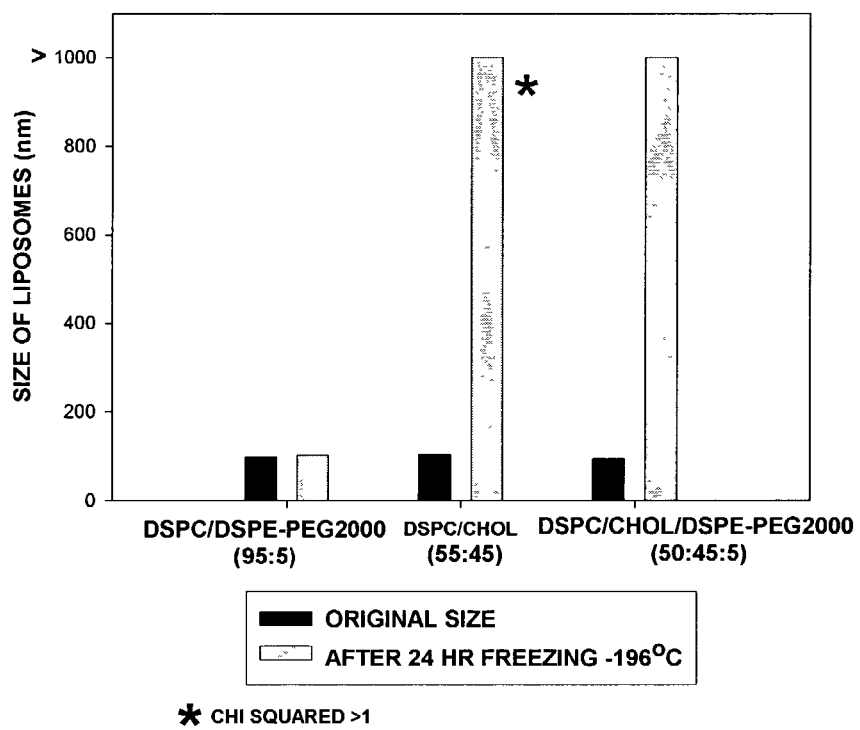
FIG. 8 is a histogram showing the size of liposomes containing 300 mM citrate buffer both inside and outside the liposomal membrane prior to (black bar) and subsequent to (grey bar) 24 hour freezing. Liposomes consisting of DSPC/

FIG. 7 shows that the size of DPPC/DSPE-PEG2000 (95:5 mol %) liposomes (cholesterol free liposomes) hydrated in 300 mM citrate did not exhibit substantial changes in size prior to and subsequent to freezing. In contrast, DPPC/chol (55:45 mol %) and DPPC/cholesterol/DSPE-PEG2000 (50:45:5 mol %) liposomes, also hydrated in 300 mM citrate, increased in size approximately ten fold subsequent to freezing. The same trend was displayed by DSPC/DSPE-PEG2000 (95:5 mol %), DSPC/chol (55:45 mol %) and DSPC/cholesterol/DSPE-PEG2000 (50:45:5 mol %) liposomes hydrated in citrate as exemplified in FIG. 8.

The size of DPPC/DSPE-PEG2000 (95:5 mol %) liposomes hydrated in HBS also did not exhibit substantial changes in size subsequent to freezing as shown in FIG. 9. In contrast, DPPC/chol (55:45 mol %) and DPPC/cholesterol/DSPE-PEG2000 (50:45:5 mol %) liposomes, also hydrated in HBS, exhibited substantial increases in size subsequent to freezing (also FIG. 9).

FIG. 10 shows that the size of DSPC/DSPE-PEG2000 (95:5 mol %) liposomes hydrated in HBS did not change subsequent to freezing whereas liposomes hydrated with HBS and consisting of DSPC/cholesterol (55:45 mol %) and DSPC/cholesterol/DSPE-PEG2000 (50:45:5 mol %) also followed the same trend as in FIG. 9.

FIG. 11 shows that liposomes consisting of DPPC/DSPE-PEG750 (95:5 mol %) and DSPC/DSPE-PEG750 (95:5 mol %) and hydrated in HBS also do not change in size subsequent to freezing thus demonstrating that low molecular weight hydrophilic polymers also protect against liposome aggregation due to freezing in the cholesterol free systems.

FIG. 12 shows that liposomes consisting of DAPC/DSPE-PEG2000 (95:5 mol %) and hydrated in HBS also did not change in size substantially subsequent to freezing thus demonstrating that increases in acyl chain length do not affect cryostability properties.

EXAMPLE 7

Cholesterol-Free pH Gradient PEGylated Liposomes Resist Aggregation Subsequent to Freezing Liposomes consisting of DPPC/DSPE-PEG2000 (95:5 mol %) and DPPC/cholesterol/DSPE-PEG2000 (50:45:5 mol %) were prepared according to the method of Example 7 (using citrate as the hydration buffer) except following extrusion and size determination, the liposomes were passed through a Sephadex G50 column equilibriated in HBS in order to generate a pH gradient. The resulting liposomes were frozen in liquid nitrogen (–196° C.) for 24 hrs, allowed to thaw at room temperature followed by a second determination of average liposome size.

FIG. 13 shows that the size of DPPC/DSPE-PEG2000 (95:5 mol %), pH gradient liposomes did not exhibit substantial changes in size subsequent to freezing. In contrast, DPPC/cholesterol/DSPE-PEG2000 (50:45:5 mol %) pH gradient liposomes, also hydrated in 300 mM citrate, increased in size approximately three fold subsequent to freezing. Likewise, as exemplified in FIG. 14, pH gradient liposomes consisting of DSPC/DSPE-PEG2000 (95:5 mol %) did not demonstrate changes in size subsequent to freezing whereas DSPC/cholesterol/DSPE-PEG2000 liposomes did.

EXAMPLE 8

Cryostability of Cholesterol-Free and Cholesterol-Containing Liposomes Comprising Encapsulated Glucose Liposomes were prepared according to Example 7 except hydration was carried out in a solution of 20 mM HEPES, 150 mM NaCl, 50 mM glucose pH 7.4 with traces of $^{14}$C-glucose. The resulting liposomes containing passively encapsulated glucose were sized and then passed through a 10 mL G50 Sephadex column in HBS to remove the glucose from the exterior medium. Percent glucose entrapment was measured by liquid scintillation counting. The liposomes were frozen at −196° C., allowed to thaw at room temperature followed by size determination using QELS analysis. Percent glucose encapsulation was measured after freezing by passing the liposomes through a 1 mL G50 Sephadex spin column equilibriated with HBS followed by scintillation counting of the eluant.

FIG. 15 shows that DPPC/DSPE-PEG2000 (95:5 mol %) liposomes containing entrapped glucose are resistant to aggregation induced by freezing. DPPC/cholesterol/DSPE-PEG2000 (50:45:5 mol %), on the other hand, increase in size subsequent to the freezing step. Conventional methods require the presence of cryoprotectants on both the inside and outside surfaces of the liposome. These results show that the presence of cryoprotectant on the inside of the liposome is sufficient for freeze/thaw protection.

Percent encapsulation of glucose before and after freezing is represented in FIG. 16. Liposomes consisting of DPPC/DSPE-PEG2000 (95:5 mol %) did not exhibit loss of glucose after freezing. In contrast, leakage of glucose after freezing occurred with liposomes consisting of DPPC/cholesterol/DSPE-PEG2000 (50:45:5 mol %).

EXAMPLE 9

Cryostability of Cholesterol-Free Liposomes Comprising Encapsulated Doxorubicin

Liposomes with transmembrane pH gradients were prepared as in Example 8. Doxorubicin was added to the liposome mixture at a 0.2:1 doxorubicin: lipid ratio and incubated for 2 hrs at 37° C. for DPPC/DSPE-PEG2000 liposomes. After incubation, the mixture was passed through a 1 mL G50 Sephadex spin column equilibriated with HBS. Lipid concentration of the eluant was measured by liquid scintillation counting. To measure levels of doxorubicin, a defined volume of the eluant was adjusted to 100 µL followed by addition of 900 µL of 1% Triton X-100 to dissolve the liposomal membrane. The sample was heated until cloudy in appearance and the Abs480 was measured after equilibration at room temperature. Concentrations of doxorubicin were calculated by preparing a standard curve.

Doxorubicin encapsulated liposomes were passed through a 10 mL Sephadex G50 column in HBS (pH 7.4) to exchange the external buffer for HBS. Lipid and doxorubicin levels were determined as above. The liposomes were frozen at −196° C. for 24 hrs followed by QELS analysis to determine the new size of the liposomes after thawing at room temperature. The liposomes were next passed through a G50 Sephadex spin column equilibriated with HBS and lipid and doxorubicin concentrations measured as above.

As depicted in FIG. 17, DPPC/DSPE-PEG2000 (95:5 mol %) liposomes encapsulating doxorubicin did not increase in size subsequent to freezing. Doxorubicin was also retained in this formulation after freezing.

EXAMPLE 10

Cryostable Cholesterol-Free Liposomes Loaded with Drug Subsequent to Freezing

Liposomes were prepared as in Example 6 and frozen for 24 hours at −196° C. A subset of the samples were loaded with doxorubicin prior to freezing ("loaded fresh") and another subset subsequent to freezing. Loading of DPPC/DSPE-PEG2000 (95:5 mol %) was carried out at 37° C. for 2 hours and at 60° C. for 15 minutes for DSPC/DSPE-PEG2000 liposomes. Determination of the percent encapsulation of doxorubicin was carried out as in Example 10. Liposomes containing cholesterol were unloadable due to aggregation. Liposomes consisting of DPPC/DSPE-PEG2000 (95:5 mol %) were loaded by incubation at 37° C. whereas liposomes consisting of DSPC/DSPE-PEG2000 (95:5 mol %) were loaded by incubation at 60° C.

FIGS. 18 and 19 show that DPPC/DSPE-PEG2000 (95:5 mol %) and DSPC/DSPE-PEG2000 liposomes loaded prior to and subsequent to freezing display similar loading profiles.

These results demonstrate that cholesterol-free liposomes may be actively loaded with agent subsequent to freezing. This allows frozen liposomes to be provided in an unencapsulated form for subsequent loading with an agent.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow. All publications or patent documents cited in this specification are incorporated herein by reference as if each such publication or document was specifically and individually indicated to be incorporated herein by reference.

Citation of the above publications or documents is not intended as an admission that any of the foregoing is pertinent prior art, nor does it constitute any admission as to the contents or date of these publications or documents.

The invention claimed is:

1. A composition comprising liposomes that contain at least one biologically active agent
    wherein the ordered bilayer(s) of said liposomes consist(s) essentially of:
    (a) one or more vesicle forming lipids, which are phospholipids or sphingolipids such that;
    (b) at least 1 mol % of said bilayer(s) is phosphatidylglycerol (PG) and/or phosphatidylinositol (PI);
    (c) 5-20 mol % cholesterol; and
    wherein said liposomes have a mean diameter between 80-200 nm +/−25 nm; and
    have a transition temperature ($T_c$) of at least 38° C.
    which composition is cryostable in the absence of cryoprotectant.

* * * * *